United States Patent
Pan et al.

(10) Patent No.: US 9,480,462 B2
(45) Date of Patent: Nov. 1, 2016

(54) MICROPATTERNED TEXTILE FOR FLUID TRANSPORT

(71) Applicant: THE REGENTS OF THE UNIVERSITY OF CALIFORNIA, Oakland, CA (US)

(72) Inventors: Tingrui Pan, Woodland, CA (US); Siyuan Xing, Davis, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 317 days.

(21) Appl. No.: 14/203,977

(22) Filed: Mar. 11, 2014

(65) Prior Publication Data

US 2014/0288515 A1 Sep. 25, 2014

Related U.S. Application Data

(60) Provisional application No. 61/780,268, filed on Mar. 13, 2013.

(51) Int. Cl.
*G01N 1/10* (2006.01)
*A61B 10/00* (2006.01)

(52) U.S. Cl.
CPC ...... *A61B 10/0064* (2013.01); *Y10T 137/0318* (2015.04)

(58) Field of Classification Search
CPC .......................... G01N 1/10; A61B 10/0064
USPC ........ 422/502, 504; 436/180; 2/69; 442/243, 442/310
See application file for complete search history.

(56) References Cited

U.S. PATENT DOCUMENTS

| | | | | |
|---|---|---|---|---|
| 4,943,522 A * | 7/1990 | Eisinger | ........... | G01N 33/54386 422/537 |
| 5,149,505 A * | 9/1992 | English | ........... | B01L 3/502 422/547 |
| 5,202,268 A * | 4/1993 | Kuhn | ........... | B01L 3/5023 422/412 |
| 5,297,296 A * | 3/1994 | Moretz | ........... | A41B 9/004 2/170 |
| 6,140,136 A * | 10/2000 | Lee | ........... | G01N 33/54366 422/423 |
| 6,187,391 B1 * | 2/2001 | Kataoka | ........... | D06M 10/025 427/209 |
| 6,821,485 B2 | 11/2004 | Beebe et al. | | |
| 6,955,999 B1 * | 10/2005 | Boye | ........... | A41D 13/0053 139/409 |
| 7,008,887 B2 | 3/2006 | Rearick et al. | | |
| 7,169,720 B2 * | 1/2007 | Etchells | ........... | A43B 1/0045 428/109 |
| 7,189,580 B2 | 3/2007 | Beebe et al. | | |
| 7,682,994 B2 * | 3/2010 | Van Emden | ........... | A41D 31/02 264/103 |
| 7,842,625 B1 | 11/2010 | Stockton et al. | | |
| 8,709,354 B2 * | 4/2014 | Bhandari | ........... | B01L 3/502707 422/502 |
| 8,806,663 B2 * | 8/2014 | White | ........... | A41D 1/00 2/69 |
| 2004/0058072 A1 * | 3/2004 | Rearick | ........... | A41D 31/00 427/324 |
| 2005/0075027 A1 * | 4/2005 | Etchells | ........... | A43B 1/0045 442/205 |

(Continued)

OTHER PUBLICATIONS

Walker, G. and Beebe, D., "A passive pumping method for microfluidic devices," Lab Chip, Aug. 5, 2002, vol. 2, pp. 131-134.

(Continued)

*Primary Examiner* — Arlen Soderquist
(74) *Attorney, Agent, or Firm* — O'Banion & Ritchey LLP; John P. O'Banion

(57) ABSTRACT

This invention includes the implementation of several unconventional droplet manipulations on a superhydrophobic-patterned surface microfluidic platform, which may be applied to automated biological analyzes and point-of-care diagnostic applications.

29 Claims, 14 Drawing Sheets

(56) References Cited

U.S. PATENT DOCUMENTS

| | | | |
|---|---|---|---|
| 2006/0127462 A1* | 6/2006 | Canada | A01N 59/16 424/445 |
| 2006/0148356 A1* | 7/2006 | Zhang | D04B 1/14 442/310 |
| 2007/0027383 A1* | 2/2007 | Peyser | A61B 5/14521 600/347 |
| 2007/0093162 A1* | 4/2007 | Holcombe | A41B 17/00 442/208 |
| 2007/0179371 A1* | 8/2007 | Peyser | A61B 5/14521 600/347 |
| 2009/0270704 A1* | 10/2009 | Peyser | A61B 5/14521 600/346 |
| 2011/0189786 A1 | 8/2011 | Reches et al. | |
| 2012/0152361 A1 | 6/2012 | Williams et al. | |
| 2012/0192952 A1 | 8/2012 | Shen et al. | |
| 2013/0019377 A1 | 1/2013 | Lambertz | |
| 2013/0095506 A1* | 4/2013 | Bhandari | B01L 3/502707 435/7.92 |
| 2014/0109282 A1* | 4/2014 | White | A41D 1/00 2/69 |
| 2015/0132742 A1* | 5/2015 | Thuo | B01L 3/502707 435/5 |

OTHER PUBLICATIONS

Xing, S., et al. "Droplet-driven transports on superhydrophobic-patterned surface microfluidics," Lab Chip, 2011, 11, pp. 3642-3648.

Owens et al., "Control of Microfluidic Flow in Amphiphilic Fabrics," ACS Appl. Mater. Interfaces, Sep. 26, 2011, 3, pp. 3796-3803.

Li et al., "Thread as a Versatile Material for Low-Cost Microfluidic Diagnostics," ACS Appl. Mater. Interfaces, Dec. 9, 2009, vol. 2, No. 1, pp. 1-6.

\* cited by examiner

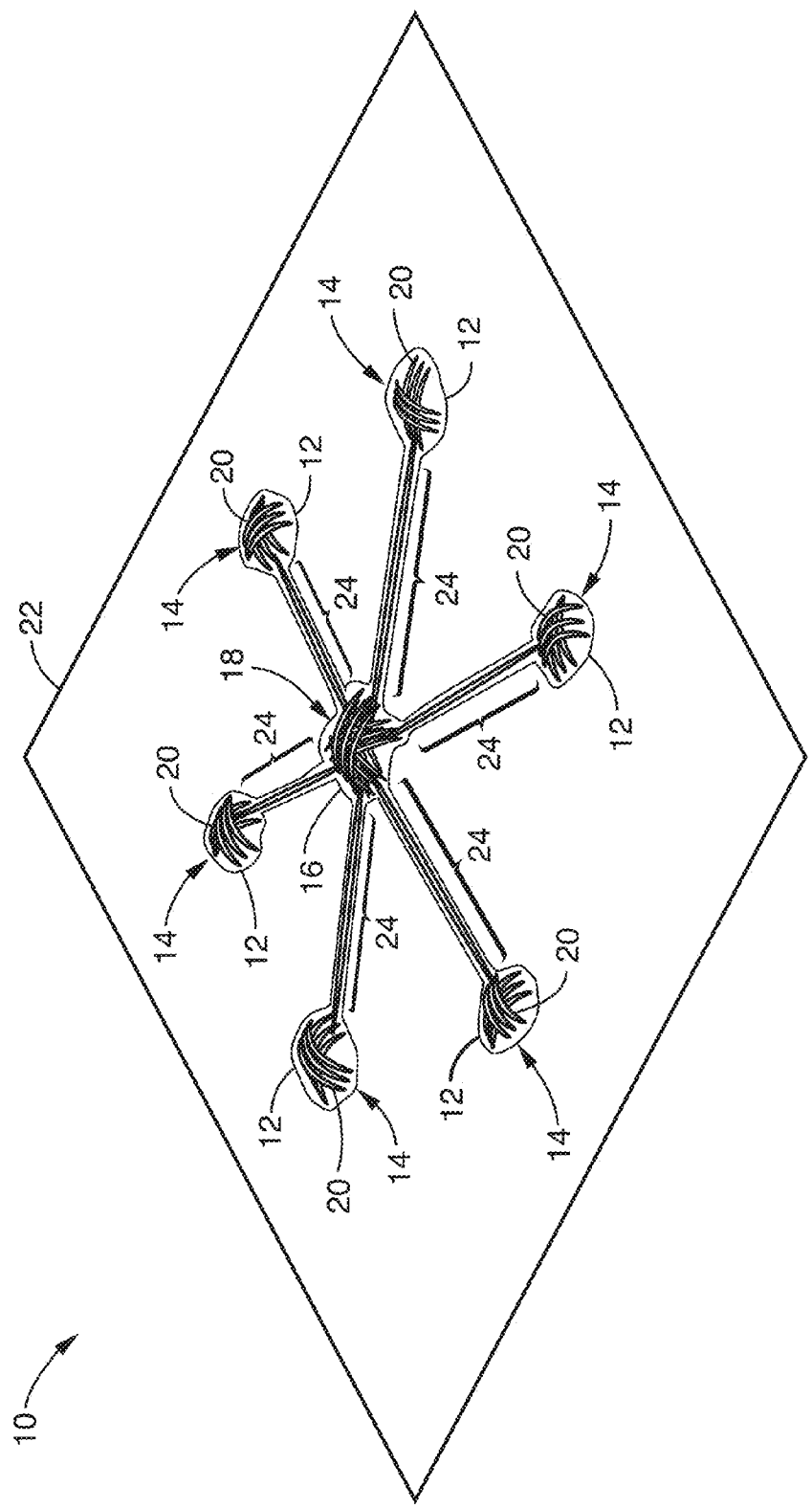

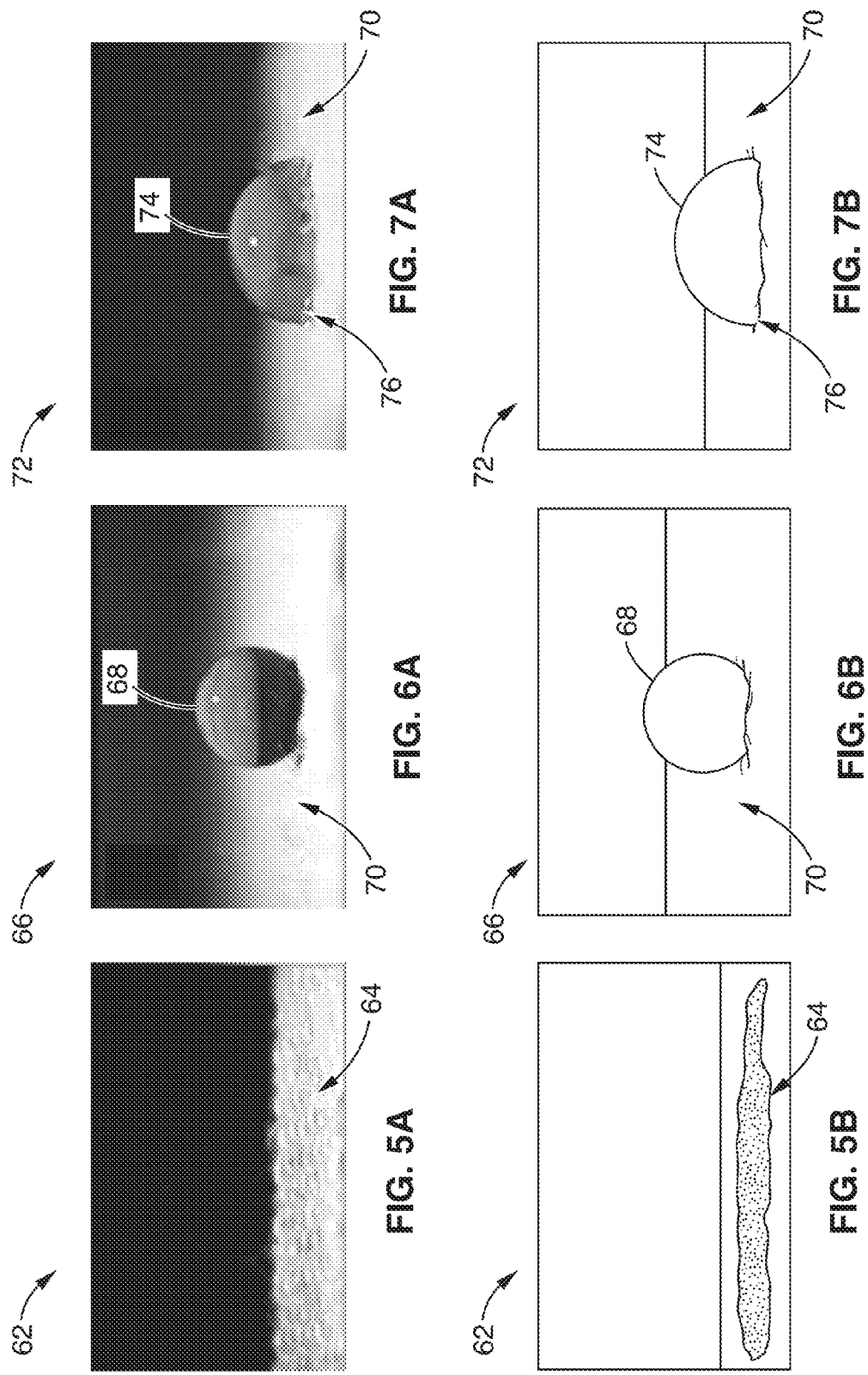

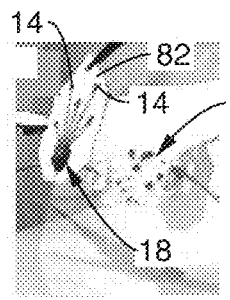 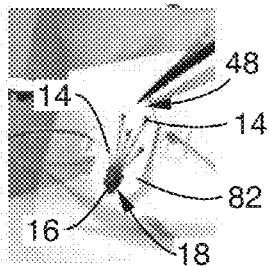 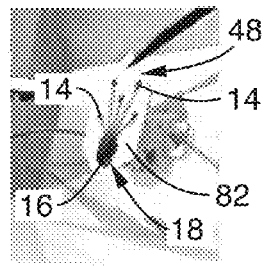 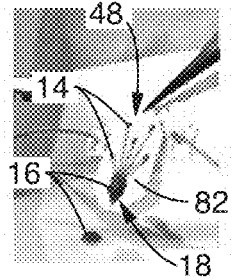
FIG. 16A　　FIG. 16B　　FIG. 16C　　FIG. 16D
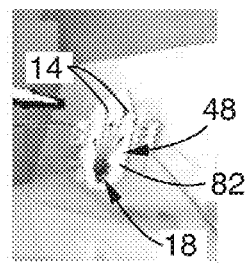 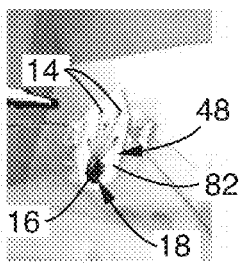 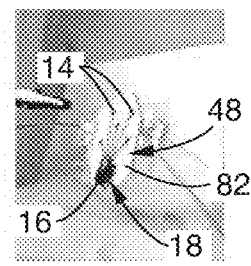 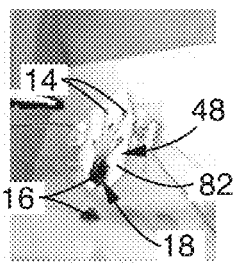
FIG. 17A　　FIG. 17B　　FIG. 17C　　FIG. 17 D

MICROPATTERNED TEXTILE FOR FLUID TRANSPORT

CROSS-REFERENCE TO RELATED APPLICATIONS

This application claims the benefit of U.S. provisional patent application Ser. No. 61/780,268 filed on Mar. 13, 2013, incorporated herein by reference in its entirety.

STATEMENT REGARDING FEDERALLY SPONSORED RESEARCH OR DEVELOPMENT

This invention was made with Government support under 0846502, awarded by the National Science Foundation. The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

Not Applicable

BACKGROUND OF THE INVENTION

1. Field of the Invention

This invention pertains generally to a superhydrophobic textile, and more particularly to a micropatterned superhydrophobic textile for biofluidic transport.

2. Description of Related Art

Microfluidics has gained increasing popularity in the handling, transporting, and analyzing of minute volumes of biological and chemical fluids. Open-surface and interfacial microfluidics, where one or more gas-liquid interfaces exist as a boundary condition, are emerging directions in microfluidics from which several new and flexible operations have been established, including self-propelled motion, three-dimensional connectivity, open sample accessibility, direct reactivity and readability, in addition to conventional microflow manipulations. Specifically, paper-based testing strips, employing the capillary force (also known as wicking force) generated by the microscopic fibrous/porous structures within the substrate, have been considered as the early historic implementation of interfacial microfluidics which are widely used in pH value indication and pregnancy testing.

The latest development of the concept of lab-on-a-paper has enabled biochemical assaying on multilayer micropatterned paper substrates fabricated by a simple printing process that form three-dimensional flow networks for multiplexed biochemical analyses (e.g., glucose, urine, and pH). In conjunction with conductive ink printing, this group has also successfully demonstrated quantitative electrochemical analysis on the paper-based devices by measuring the concentrations of heavy metal ions and glucose molecules.

More recently, the interfacial microfluidic concept has been extended to textile-based structures and surfaces (e.g., yarns and fabrics). Textile-based microfluidics utilize a similar wicking force as seen in paper that is produced by hydrophilic yarns (e.g., cotton yarns) to direct biological reagents along the fibrous structure which affords the aforementioned operational capacities of interfacial microfluidics while providing a low-cost and scalable solution based on well-established, traditional textile manufacturing techniques such as automatic weaving, knotting, and stitching. In particular, basic microfluidic functions, including pumping, mixing, separation, and networking, have been recently demonstrated on knotted yarn structures. Although the current development of capillarity-enabled interfacial microfluidics holds great promise to biofluidic manipulation, its intrinsically driven mechanism continues to be a major challenge for continuous and facilitated biofluidic transport. For instance, an external fluidic driver (e.g., capillary or syringe pumps) still remains necessary to provide continuous flow on the fabric network.

Competitive fabrics, featuring quick drying, such as Cool-Max, utilize polyester fibers with irregular cross-sections to wick liquid from the surface of human skin and to spread the liquid to enhance evaporation. The only driving force is still capillary force, which diminishes when lots of liquid wets the surface. Once the textile is wetted with sweat, the gas permeability decreases and the weight increases. Moreover, the evaporation of the sweat is highly affected by the environmental humidity.

BRIEF SUMMARY OF THE INVENTION

Accordingly, the latest efforts for implementing surface tension-driven flow on the interfacial microfluidics have enabled a new approach to automated microflow operations. By harvesting Laplace pressure gradients from various sizes of liquid droplets, self-propelled flow in an open-channel configuration was achieved. Importantly, a surface tension-driven micropump can be achieved simply by lithographically defining hydrophilic flow paths on a superhydrophobic substrate to provide extensive pumping capacity, flexible pumping rates, as well as bidirectional control.

Textile-enabled interfacial microfluidics, utilizing fibrous hydrophilic yarns (e.g., cotton) to guide biological reagent flows, has been extended to various biochemical analyses recently. The restricted capillary-driving mechanism, however, persists to be a major challenge for continuous and facilitated biofluidic transport. In the subject invention, a novel interfacial microfluidic transport principle is described to drive three-dimensional liquid flows on a micropatterned superhydrophobic textile (MST) platform in a more autonomous and controllable manner.

Specifically, the MST system utilizes the surface tension-induced Laplace pressure to facilitate the liquid's motion along the hydrophilic yarn, in addition to the capillarity present in the fibrous structure. The fabrication of MST is accomplished by simply stitching hydrophilic cotton yarn into a superhydrophobic fabric substrate (contact angle 140±3°), from which well-controlled wetting patterns are established for interfacial microfluidic operations. The geometric configurations of the stitched micropatterns, e.g., the lengths and diameters of the yarn and bundled arrangement, can all influence the transport process. The surface tension-induced pressure as well as pumping speed can be highly controllable by the sizes of the stitching patterns of hydrophilic yarns and the confined liquid volume. The MST can be potentially applied to large volume and continuous biofluidic collection and removal.

Two operation modes, discrete and continuous transports, are also provided. In addition, the gravitational effect and the droplet removal process have also been considered and quantitatively analyzed during the transport process. In one embodiment, an MST design has been implemented on an artificial skin surface to collect and remove sweat in a highly efficient and facilitated means. The results have illustrated that the novel interfacial transport on the textile platform can be extended to a variety of biofluidic collection and removal applications.

This invention provides a new mechanism for removing liquid from the skin's surface by surface tension and merging of droplets. This mechanism stabilizes the transport rate that will not be affected by the moisture level of the fabric or environmental humidity. The superhydrophobic property of the fabric ensures the dryness of most of the skin's surface area and excellent air permeability. Moreover, since the liquid is not absorbed by most regions of the textile, the weight of the fabric remains light during the perspiration process. Additional features such as self-cleaning and waterproofing are also not available in former functional fabrics.

By way of example and not by limitation, the subject invention includes a novel type of textile that is able to transport sweat on the skin's surface to the outer sides of the fabric, where the liquid collects and drips off. The textile utilizes interfacial microfluidic principles and implements liquid transport spontaneously by micropatterns on the surface of superhydrophobic fabric. Embodiments of the invention provide a new dimension of transport to the textiles using surface tension force, in addition to the intrinsic capillary force in hydrophilic fibers. Several new features are present in this invention. For example, this is the first time that interfacial/surface microfluidics principles have been applied to body fluidic transport. Body fluid removal is facilitated through a well controlled flow rate and removal rate. The patterned wettability can handle both moisture and liquid removal. The textile is also self-cleaning and waterproof.

Accordingly, one aspect of the invention provides a means of fast sweat removal. This structure of hydrophilic material on a superhydrophobic substrate can quickly remove the sweat from the skin and transport it to the outside of the fabric, while keeping most areas dry and gas-permeable.

Another aspect of the invention provides an alternative to a diaper or maxi pad. This structure can facilitate bio-fluids to be uniformly distributed in the absorbent material and prevent leakage.

Another aspect of the invention provides a means of wound dressing for high-exudate wounds or chronic wounds. This structure can quickly transport the exudate from the wound to the outside of the dressing and remain gas permeable to the wound.

Another aspect of the invention provides a textile-based microfluidic chip. This provides an ideal structure for fabrication of low-cost microfluidic devices, for example, pregnancy test strips.

Another aspect of the invention provides a water collection network. This can be done by suspending this material in a high-humidity environment and allowing water droplets to condense on a network of hydrophilic channels.

Yet another aspect of the invention provides for water-oil separation by immersing this material in a water-oil mixture. The water droplets dispersed in the oil can be merged and collected.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 1 is a diagram of a fluidic network design in a radial pattern (multi-inlet-single-outlet) on the MST platform using the autonomous interfacial transport concept according to one embodiment.

FIG. 5A is an image of the wetting and transport phenomena of MST: a 5 µL droplet sits on an original hydrophilic stitching substrate.

FIG. 5B is a schematic diagram of FIG. 5A.

FIG. 6A is an image of the wetting and transport phenomena of MST: a 5 µL droplet sits on a superhydrophobic treated substrate.

FIG. 6B is a schematic diagram of FIG. 6A.

FIG. 7A is an image of the wetting and transport phenomena of MST: a 5 µL droplet sits on a 2 mm circular hydrophilic micropattern.

FIG. 7B is a schematic diagram of FIG. 7A.

FIG. 16A through FIG. 16D are images of the 3D discrete transport mode of the MST from FIG. 15A and FIG. 15B on the artificial skin model.

FIG. 17A through FIG. 17D are images of the continuous transport mode of the MST from FIG. 15A and FIG. 15B on the artificial skin model.

DETAILED DESCRIPTION OF THE INVENTION

I. Introduction

Figure 2A:
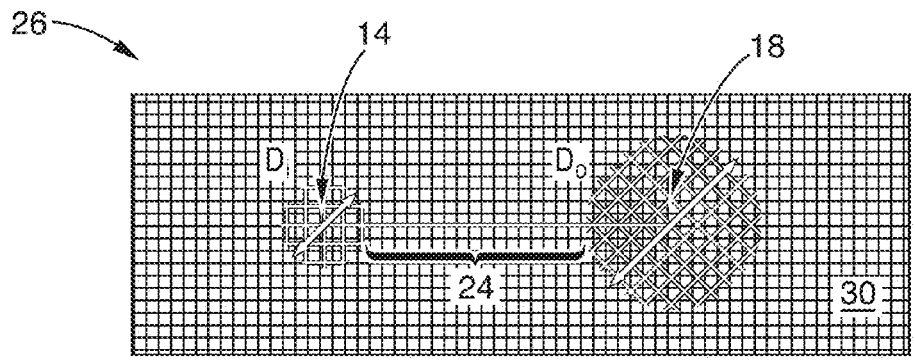
FIG. 2A is a schematic diagram of a top view of a fluid flow path on MST.

In recent decades, superhydrophobicity, also known as the remarkable water-repellent Lotus effect mimicked from nature, has been introduced to functional fabric development (e.g., water-repellent and anti-icing coatings). A number of convenient and robust manufacturing techniques have been implemented on various fabric materials to impart superhydrophobicity. For instance, a facile approach has been established using silica nanoparticles with fluorosilane modification on cotton-based fabrics, from which a water contact angle (CA) as high as 155°±2° has been repetitively achieved. Similar water repellence (CA>150°) has been implemented on non-woven nylon fabrics by sequentially grafting polyacrylic acid (PAA) and fluoroamine molecules onto the original cloth.

Similarly, superhydrophilic textiles can be achieved in a comparable manner. For example, wool-based fabrics can be rendered superhydrophilic by depositing a thin layer of silica particles of 27 nm in diameter onto the textile. Furthermore, patterned hydrophobicity on fabric structures has also been investigated. An alternatively woven textile from both hydrophobic and hydrophilic yarns has been used to illustrate the capacity of autonomous water-oil separation. Moreover, predefined microfluidic channels woven by wetting and non-wetting silk yarns have been utilized for immunoassays. Similarly, pH sensing has been achieved by soaking the aqueous samples through amphiphilic channels created by selective surface modifications.

According to the following embodiments, an interfacial microfluidic transport principle to establish three-dimensional liquid flows on micropatterned superhydrophobic textiles (MST) in an autonomous, controllable and continuous fashion is presented. As the central concept, the interfacial microfluidic transport utilizes the surface tension-induced pressure gradient along the flow path defined by extreme wetting contrast to facilitate the liquid motion in the MST network in addition to the capillarity presented in the fibrous structure. The wetting contrast patterns are defined by stitching patterns of hydrophilic yarns (CA=0°) on the superhydrophobic textile (CA=140°) treated by coating a thin layer of fluoropolymer microparticles. The transport duration on MST can be highly-controlled by the dimensions of the hydrophilic pattern (inlet and outlet) and connecting yarns (channel).

Furthermore, two operation modes are provided for biofluidic transport: a) discrete transport—periodically adding a fixed volume of droplets to the inlet, and b) continuous transport—feeding a continuous flow to the inlet. In addition, a flow conductance model on different geometric patterns of yarns has also been analyzed (single yarn vs. yarn bundles) from which the microflow profiles on fibrous linear yarns can be interpreted.

Referring more specifically to the drawings, for illustrative purposes several embodiments of the system scheme of the present invention and the associated methods are depicted generally in FIG. 1 through FIG. 18C. It will be appreciated that the methods may vary as to the specific steps and sequence and the apparatus architecture may vary as to structural details, without departing from the basic concepts as disclosed herein. The method steps are merely exemplary of the order that these steps may occur. The steps may occur in any order that is desired, such that it still performs the goals of the claimed invention.

Referring now to FIG. 1, in one embodiment of the subject invention, a fluidic network design in a radial pattern 10 has been demonstrated to continuously extract inlet droplets 12 from six inlets 14 into one big outlet droplet 16 at the central outlet 18, which shows the highly-efficient transport and collection capacity of the MST in this embodiment. FIG. 1 illustrates a multi-inlet 14 single-outlet 18 yarn (or single thread or thread bundle) 20 design on the MST platform with a superhydrophobic-treated fabric substrate 22 using the autonomous interfacial transport concept. A fluidic network design 10 in a radial pattern simultaneously and continuously extracts inlet droplets 12 (each with a volume of 5 μL) from six small inlets 14 (2 mm) and merges them via channels 24 into one big outlet droplet 16 at the central outlet 18 (6 mm). The interfacial fluidic network design in a radial pattern 10 on MST may be applied to large volume and continuous biofluidic (e.g., sweat or urine) collection and removal. In comparison with current fabrics, the MST possesses high-efficiency in liquid transport while maintaining its high gas permeability from superhydrophobicity.

II. Theoretical Analysis

The MST design utilizes hydrophilic yarns micro-stitched on the superhydrophobic textile which possesses a very high CA (typically greater than 140°) and inherently low hysteresis. Once hydrophilic micropatterns are formed on the superhydrophobic textile, the extreme wetting contrast enables immobilization of the triple line of gas/liquid/solid phases along the pattern boundaries. Therefore, the internal pressure (ΔP) of any droplet deposited on MST can be directly related to its original volume (V) and the size of the hydrophilic pattern (of diameter D if circular) as described in the following equations derived from the classic Laplace's Law:

$$\Delta P = \frac{16 h \gamma}{D^2 + 4h^2} \quad (1)$$

$$V = \frac{\pi}{24}(4h^3 + 3hD^2) \quad (2)$$

where h is the height of the droplet and γ is the surface tension of the fluid.

Figure 2B:
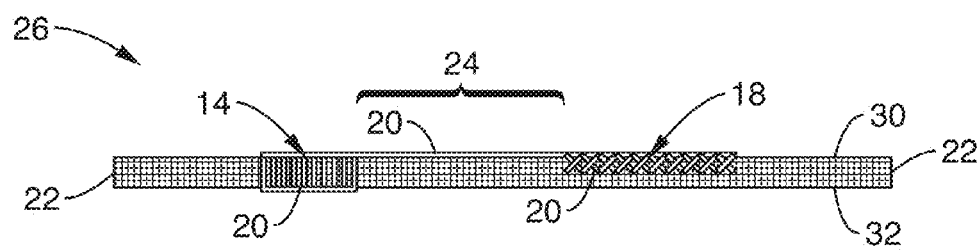
FIG. 2B is a schematic diagram of a side view of a fluid flow path on MST.

Turning now to FIG. 2A through FIG. 2D, it is shown that by connecting two reservoirs (i.e. an inlet 14 and an outlet 18) through a hydrophilic channel 24, comprising for example single threads, thread bundles, a cotton yarn or glass fiber, a simple surface-tension driven microfluidic system can be devised. FIG. 2A shows a top view of a single fluid flow path 26 with the inlet 14, outlet 18 and channel 24 connecting them. FIG. 2B is a side view of the fluid flow path 26 that shows how the inlet 14 is formed by stitching the thread or yarn 20 throughout the fabric substrate 22 (an embodiment of the MST superhydrophobic-treated fabric substrate of FIG. 1) while the outlet 18 is formed by stitching the thread 20 only on the outer surface 30 of the fabric substrate 22 and not on the inner surface 32 (e.g. the surface in contact with skin). Once the surface tension-induced pressure gradient is established along the fluid flow path 26, the liquid at the inlet 14 (of the diameter $D_i$) is automatically directed towards the outlet 18 (of the diameter $D_o$) via the hydrophilic channel 24 (i.e., the yarn). Given its laminar nature, the flow rate is approximately proportional to the Laplace pressure difference between the inlet 14 and outlet 18, but inversely proportional to flow resistance of the thread 20.

Figure 2C:
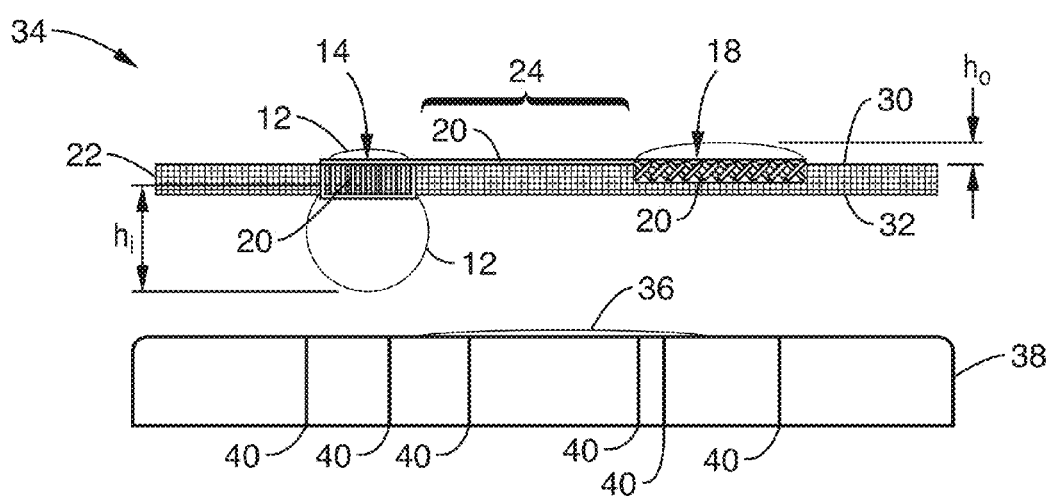
FIG. 2C is a schematic diagram of a side view of the discrete transport mode.

Based on the transport model of MST, two three-dimensional (3D) microfluidic operations have been proposed and analyzed. FIG. 2C shows a side view of the first mode, referred to as the discrete transport mode 34. The discrete transport mode 34 is established as collecting individual aqueous droplets 36 periodically from a contact surface 38 (e.g. skin) with channels or pores 40 underneath the inlet 14 of the fluid flow path 26. This operation is analogous to a charging/discharging capacitor in electronic circuitry. The inlet droplet 12 volume and reservoir size determine the radius of curvature and the corresponding Laplace pressure of the inlet droplet 12 under the high wettability contrast, which drive the collected inlet droplet 12 towards the outlet 18 on the other side. Thus, the droplet hydrodynamics can be uniquely determined by the initial conditions, as shown in FIG. 2C.

Figure 2D:
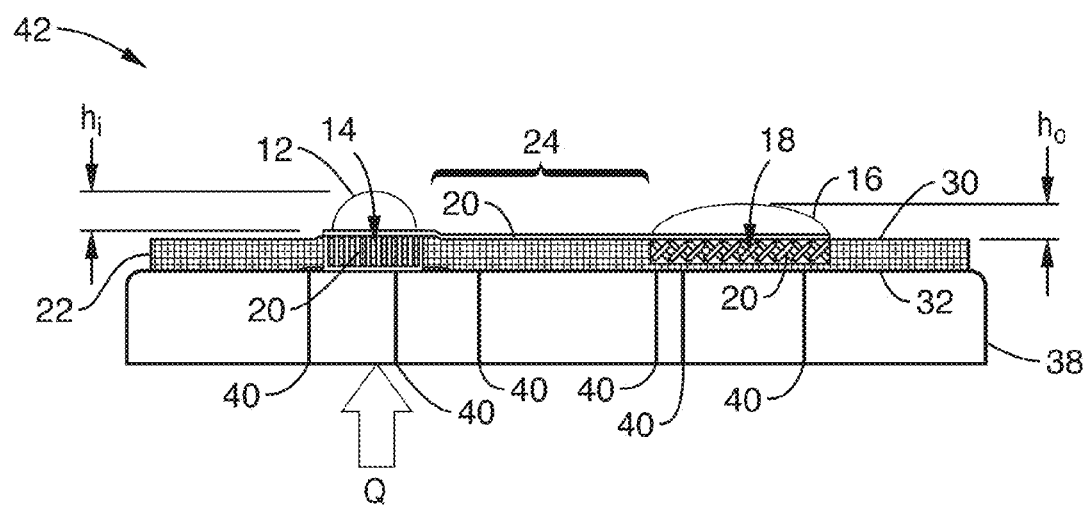
FIG. 2D is a schematic diagram of a side view of the continuous transport mode.

FIG. 2D shows a side view of the second mode, known as the continuous transport mode 42, which occurs when the fluid flow path—and MST structure 26 of FIG. 2B is in close proximity to a contact surface 38 under pressure. When a continuous inflow (Q) is perfused to the inlet 14 from the surface contact on the inside layer 32 of the fabric substrate 22, the inlet droplets 12 (fluid), while restricted to the hydrophilic fabric patterns, will be directed towards the outlet 18 on the outer surface 30 of the double-layer fabric substrate 22. This embodiment is analogous to an electronic circuit powered by a current source. It is worth noting that the maximal flow rate under this mode is set by the largest pressure gradient produced by the inlet 14, equal to the Laplace pressure in a hemispherical inlet droplet 12 of the size of the inlet 14 reservoir. Otherwise, it could lead to outflow instability.

Both modes have been characterized experimentally, in which various sizes of yarn patterns have been paired to form the self-propelled flow pump by collecting moisture from the underlying contact surfaces. Priming of the yarn patterns prior to the measurement becomes necessary to eliminate influences from capillarity. To analyze the transport parameters, a video-camera (of a 1920×1080 pixel resolution at 60 fps) installed on a stereomicroscope (Omano) was used to record the transport processes on MST. From these recordings, the elapsed times and the droplet shapes can be directly analyzed, and as a result, both the average flow rates (based on the volume change over time) and Laplace pressures inside droplets (according to the radius of curvature) can be computed accordingly.

III. Materials and Methods a. Hydrophilic Cotton Yarns

Commercially available mercerized cotton yarns with a nominal diameter of 500 μm were purchased online (100% Mercerized ELS Cotton, Star®). However, these cotton yarns came with a layer of wax on the surface and cannot be easily primed with aqueous solutions. Therefore, a hydrophilic pre-treatment (degumming) process becomes necessary to remove the outer wax shielding. First, an aqueous solution, composed of sodium carbonate (1.5% wt) and hand soap (which is mainly composed of sodium laureth sulfate and ammonium lauryl sulfate, 1.5% wt), was prepared and boiled at 300° C. on a hotplate. Subsequently, the waxed yarns were immersed into the boiled bath for 60 minutes, followed by a complete washing in deionized water at room temperature.

b. Superhydrophobic Fabric

Superhydrophobic fabric substrates were prepared from off-the-shelf cotton fabrics. The woven cotton fabrics (Fabric Flair®) composed of two layers of mesh with 31 threads per inch were purchased from a local fabric store. Commercially available superhydrophobic coating (Fluoropel™ M1604V, Belsville) was obtained from Cytonix Company and spray-coated onto the cotton fabrics of a 3 cm² surface area by an airbrush at the pressure of 50 kPa. The coating thickness can be controlled by the volume of the treatment solution per unit surface area. To achieve complete coverage with optimal superhydrophobic performance, 2 mL of the coating solution was applied and coated onto the substrate. A reduced amount of the superhydrophobic coating can be used to achieve a similar superhydrophobicity. However, it may not be as durable and robust as a thicker coating. Subsequently, a thermal curing step was performed in a 100° C. convection oven for 30 minutes, during which time the cotton fabric was temporarily fixed to a flat, rigid surface (e.g., a 5 mm-thick glass plate) to prevent any possible heat-induced curvature.

c. Characterization of the Surface Wettability

Superhydrophobicity of the treated fabric was characterized by conventional contact area (CA) measurement. A 5 μL de-ionized water droplet was deposited onto the textile surface by a micropipette, where the profile of the droplet was recorded horizontally by a stereomicroscope equipped with a DSLR CCD camera (Rebel T3, Canon). The contact areas of the droplets were assessed from the photos with graphic software (e.g. CorelDraw). An average CA value was calculated from the measurements of three droplets deposited on different spots on the same surface. The hydrophilicity (in terms of CA) of cotton yarns was measured by laying a mesh of fibers on a superhydrophobic substrate, followed by depositing a DI water droplet on the surface.

d. 3D Microfluidic Networks Fabricated by Stereo-Stitching

Figure 3A:
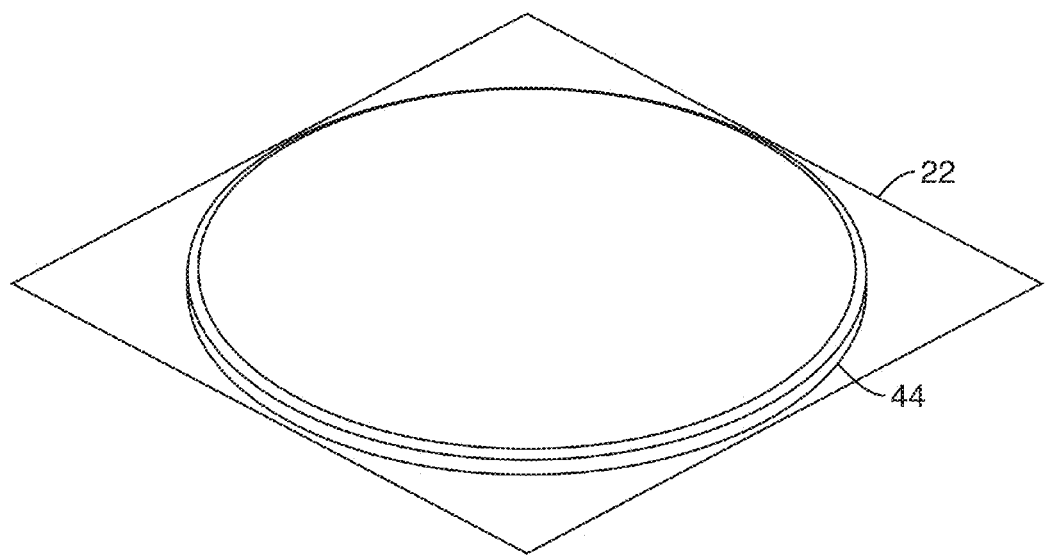
FIG. 3A through FIG. 3D are schematic diagrams of the fabrication process of MST with a multi-inlet-single-outlet design.
Figure 3B:
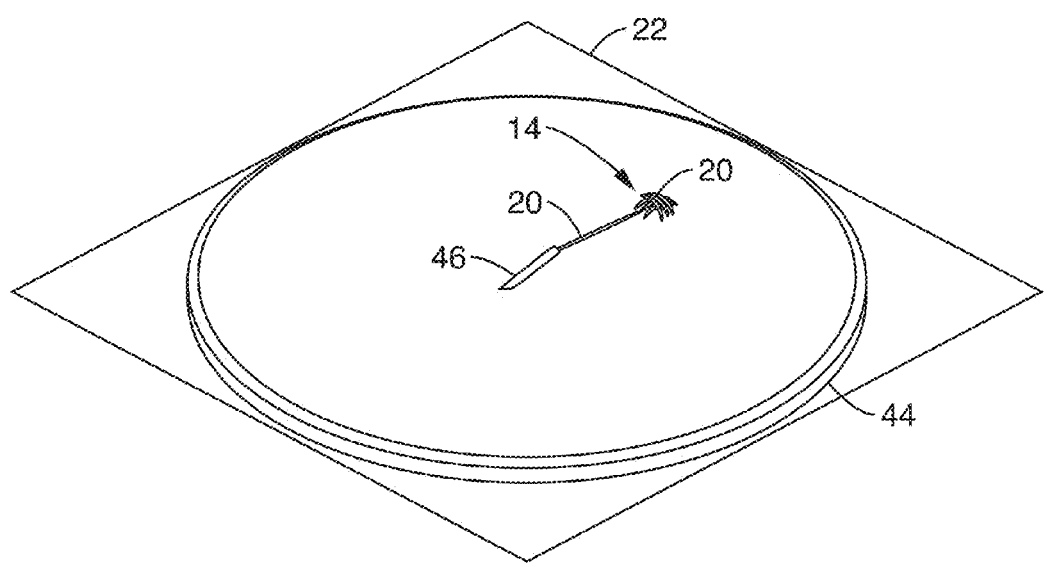
Figure 3C:
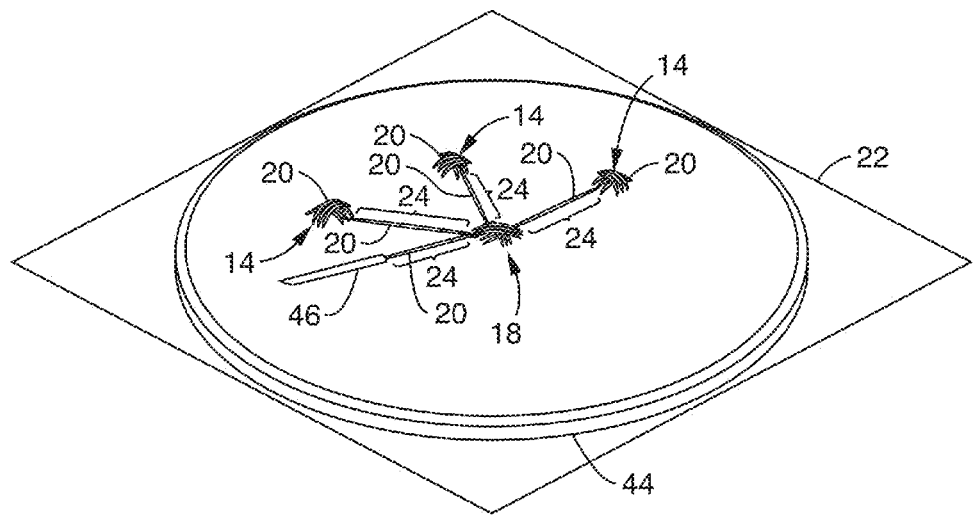
Figure 3D:
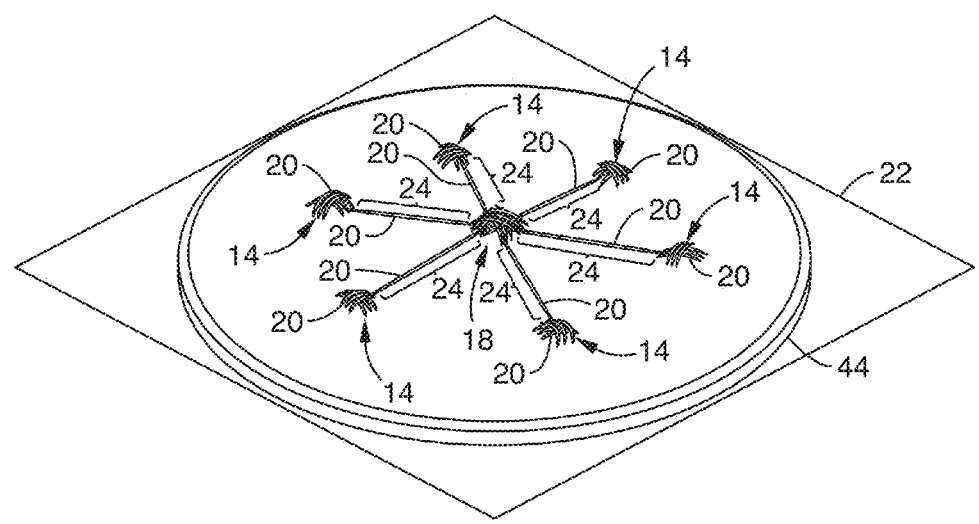

Referring now to FIG. 3A through FIG. 3D, several fluid flow paths 26 (see FIG. 2B) were formed by stitching treated hydrophilic cotton yarn 20 on the superhydrophobic-treated fabric substrate 22 to create a fluidic network design in a radial pattern 10 (see FIG. 1 and FIG. 3D). Prior to the stitching, the superhydrophobic-treated fabric substrate 22 was fixed flat under tension using an embroidery hoop 44 (4 inches in diameter). A 28 gauge stitching needle 46 (0.362 mm in diameter) was used to sew cotton yarn 20 to form the fluid flow paths 26. In order to achieve the 3D flow profile, a two-stage stereo-stitching technique, involving both penetrating and parallel stitching, was utilized to build the 3D hydrophilic structures in the inlet 14 and the outlet 18 (see also FIG. 2B). Specifically, an inlet 14 was fabricated by closely stitching the yarn 20 to penetrate through the superhydrophobic-treated fabric substrate 22 in a defined area until the fabric substrate 22 was fully covered by the yarn 20. Alternatively, an outlet 18 was fabricated by stitching the yarn 20 in parallel through the meshes only presented in the outer surface 30 (or top layer) of the fabric substrate 22. As a consequence, the hydrophilic yarns 20 of the outlet 18 were only exposed to the outer surface 30 surface of the superhydrophobic fabric substrate 22, which left the inner surface 32 still covered with the superhydrophobic fabric substrate 22. Following connecting the outlet 18 and inlet 14 micropatterns through cotton yarn 20 channels 24, a 3D hydrophilic fluid flow path 26 was formed by the two-stage stereo-stitching technique.

e. Characterization of the Flow Resistance

A continuous transport mode 42 setup (see FIG. 2D) was devised to characterize the flow resistance of the hydrophilic cotton yarn 20 on the superhydrophobic fabric substrate 22 in different configurations. A simple capillary pump was constructed from two hydrophilic glass slides (75 mm×50 mm×1 mm) separated by two 370 µm-thick Polydimethylsiloxane (PDMS, Sylgard 184, Dow Corning; 10:1 base:crosslinker) spacers to generate a constant negative pressure head. According to the Laplace equation, the capillarity-induced pressure gradient was 394.5 Pa and matched well with our experimental observation (less than 4% deviation). During the flow resistance test, the cotton yarn 20 was placed on a superhydrophobic textile (fabric) substrate 22 and connected between the primed capillary pump and a small reservoir. The flow rate was calculated based on the transport (or depletion) time of a known volume from the reservoir assuming that the hydrostatic pressure in the reservoir could be ignored. Each data point was measured in triplicate.

f. Fabrication of Artificial Skin Model

In another embodiment of the subject invention, to demonstrate the utility of the interfacial microfluidic transport, a newly established MST structure was applied to sweat removal on artificial human skin. One of the major advantages of using the MST for sweat removal is that the superhydrophobic fabric substrate 22 is only covered by a limited patterned area of highly wettable yarn 20, while achieving a high sweat removal rate on the hydrophilic fluid flow path 26 and maintaining high gas permittivity on a majority of the superhydrophobic region. Implemented by using the 3D stitching technique, sweat collection areas can be limited to a small fraction of the skin surface while a majority of surface microfluidic networks are running on the exterior fabric surface, in contrast to existing moisture-wicking fabrics. Accordingly, the interfacial microfluidics-enabled textile possesses high-efficiency in sweat transport and removal while maintaining low humidity and high gas permeability during intense sweating.

Figure 4A:
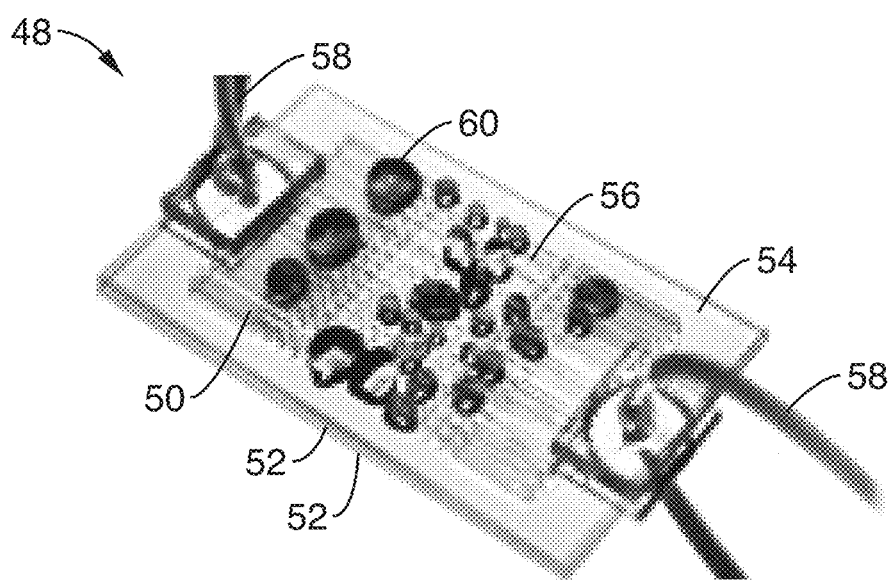
FIG. 4A is an image of the artificial skin model.
Figure 4B:
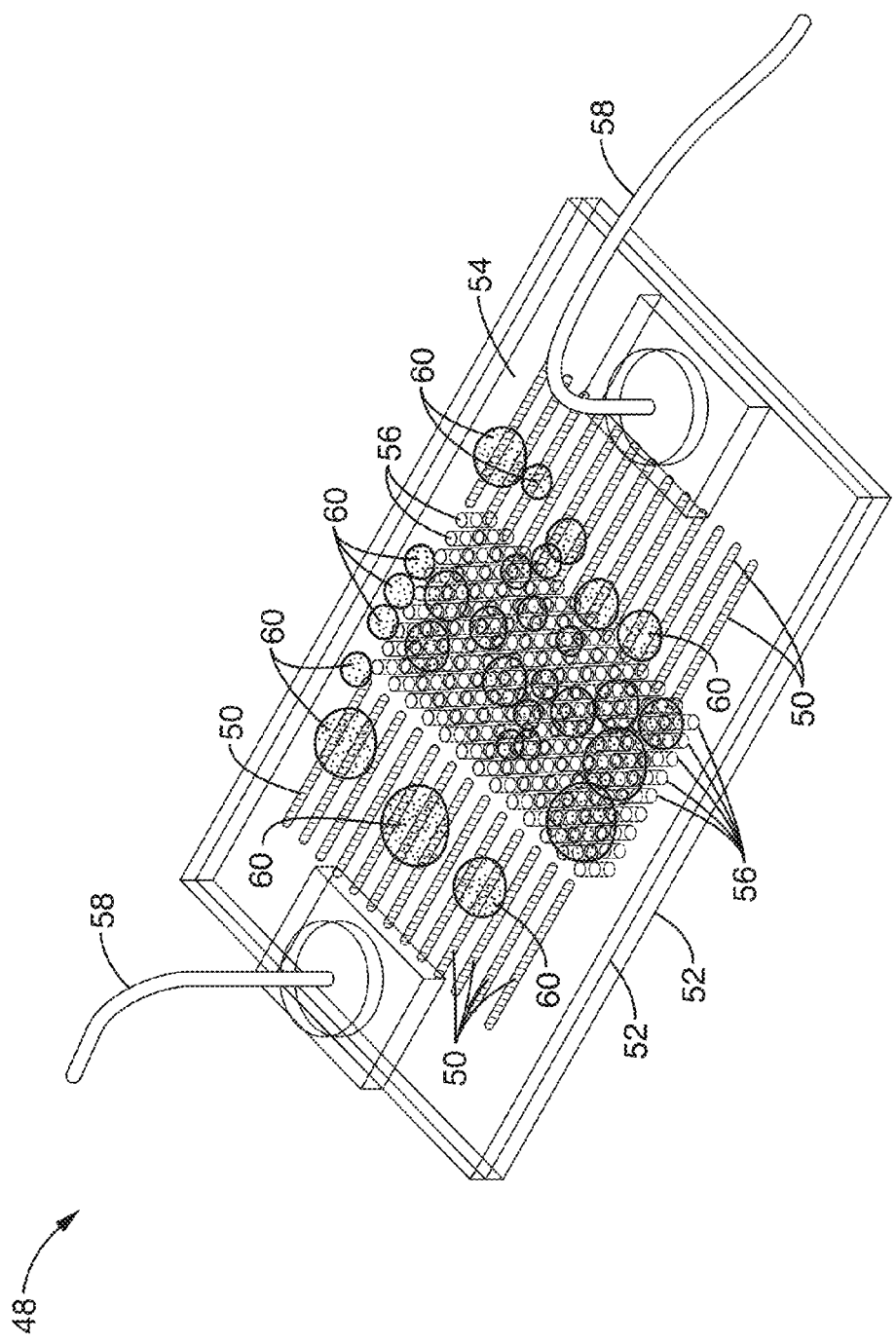
FIG. 4B is a schematic diagram of the artificial skin model.

Referring now to FIG. 4A (image) and FIG. 4B (schematic), the artificial skin model 48 was devised on a 3-layer microfluidic structure. Microchannels 50 were cut into the bottom two pieces 52 and the top layer 54 was perforated with pores 56. The diameter and density of the pores 56 were 60 µm and 114 pores/cm$^2$, respectively, similar to the opening and density of human sweat glands on human backs (160±30 glands/cm$^2$). The device was fabricated from PDMS using a simple laser micromachining PDMS approach. In brief, thin layers of PDMS (Sylgard 184, Dow Corning; 10:1 base:crosslinker) were prepared by spin-coating on a clean glass slide, followed by post-baking on a 100° C. hotplate for 15 minutes. Subsequently, a desktop $CO_2$ laser machine (VersaLaser, Universal Laser Systems) directly engraved the designed microchannels 50 and pores 56 on the PDMS substrates with control parameters preset in the software panel. After cleaning each piece in ethanol, the three layers of PDMS were aligned aided by a mask aligner (ABM, Inc.) and compressed to bond the chip using PDMS's inherent adhesion. Finally, a syringe pump (not shown) was connected through tubes 58 and micro droplets 60 were generated on the surface to mimic the perspiration process at different flow rates.

g. Characterization of the Wetting Properties

In order to characterize the wetting properties of a fabric, four important parameters were measured, including the thickness, weight, electrical resistance (indicating the moisture level in the fabrics) and gas permeability. Specifically, the thickness of a fabric was measured by a linear gauge (EG-225, Ono Sokki) and the weight of the fabric was measured by an analytical balance (Classic Plus, Mettler Toledo). A multimeter (34401a, Agilent) was utilized to measure the electrical resistance on the fabric surface in a two-probe configuration. The resistance value was recorded once the probe tips formed an intimate contact on the fabric surface at a 3 mm separation. The average resistance was calculated from 9 measurements in different positions evenly distributed throughout the entire fabric. Moreover, the gas permeability of the fabric was evaluated by a constant gas flow setup. A rigid plastic tube of 2 cm in the inner diameter was utilized as the flow guiding channel, of which one end was connected to a pressurized gas task and a manometer (Sper Scientific). On the other end, the fabric was clamped by an elastic ring to seal the outlet, ensuring the gas flow completely passing through the textile. The gas velocity was measured by a vaneometer (Dwyer Instrument). All the weight, resistance and gas permeability assessments of each fabric were conducted before and after the fabrics were fully wetted. The wetting condition was simulated on the artificial skin surface, where a constant liquid flow was applied until the fabric became completely wetted and the measurements were repeated to record the changes between the dry and wet states.

IV. Results and Discussion

Fluidic network designs defined by the high wetting contrast between the superhydrophobic fabric substrates 22 and the hydrophilic yarns 20 provide a direct means to manipulate the internal Laplace pressure of liquid droplets, which can be utilized as a propulsion mechanism in interfacial microfluidic networks in addition to the intrinsic capillarity. In the following sections, the wettability of the MST will be discussed first, followed by characterization of the autonomous bi-droplet (single-inlet-single-outlet) transport on MST. Complete analyses on hydrophilic fluid flow paths 26 in different yarn configurations were included in the experiments. Furthermore, the distinct transport modes, discrete 34 and continuous 42 modes, will be demonstrated and characterized, followed by a discussion of the benefit of the multi-inlet-single-outlet structure. As a demonstration, an autonomous transport on MST has been performed on an artificial skin surface for rapid collection and removal of biofluid (e.g., sweat).

a. Micropatterned Superhydrophobic Textile

The off-the-shelf cross-stitching fabric, originally made from natural cotton, is hydrophilic. In addition, the inter-stitching spaces between cotton yarns form small capillary channels that provide strong wicking forces to aqueous solutions. FIG. 5A shows an image 62 of a 5 μL water droplet that has been rapidly absorbed into the hydrophilic cotton fabric substrate 64. FIG. 5B is the schematic representation of the image 62 in FIG. 5A. To alter wettability on the hydrophilic cotton fabric substrate 64, a superhydrophobic surface coating was applied to the hydrophilic cotton fabric substrate 64. A suspension of perfluoropolyether (PFPE) microparticles (of 4~8 μm in diameter) was prepared as the surface coating material for the chemical inertness and microscopic topology. After the spray-coating, the microparticles were physically absorbed onto the surface of the hydrophilic cotton fabric substrate 64, rendering the surface superhydrophobic with a water CA of 140±3°. As can be seen in the image 66 of FIG. 6A, a water droplet 68 of 5 μL maintained a nearly spherical shape on the superhydrophobic-treated cotton fabric substrate 70. FIG. 6B shows the schematic representation of the image 66 in FIG. 6A.

As described previously, hydrophilic yarns 20 with a CA close to 0° were stitched onto a superhydrophobic fabric substrate 22, forming highly wettable fluid flow path 26 micropatterns. FIG. 7A shows an image 72 of a 5 μL droplet 74 that was deposited onto a 2 mm circular hydrophilic pattern 76 and forms a semi-spherical shape as its boundary is pinned along the wetting-contrast pattern, i.e., the solid/liquid/gas triple line. Although this configuration is similar to the surface microfluidic setup fabricated by laser micromachining in our previous investigation, all the components used in the MST are obtained as off-the-shelf textile components instead. FIG. 7B shows a schematic representation of the image 72 in FIG. 7A.

The bi-droplet transport can be extended to MST by connecting two circular reservoir (e.g. inlet and outlet) patterns (2 mm to 6 mm) through a hydrophilic yarn (10 cm) flow path, demonstrating the bi-droplet surface-tension driven transport on MST. Under the wetting contrast and the induced triple line pinning, a droplet placed in each end can form a specific radius of curvature, which is established by the droplet volume (V) and reservoir diameter (D). As a result, the Laplace pressure inside each droplet can be uniquely determined. According to fluid dynamics, the droplet with higher internal pressure will be pumped simultaneously toward the droplet at the other end.

Figure 8A:
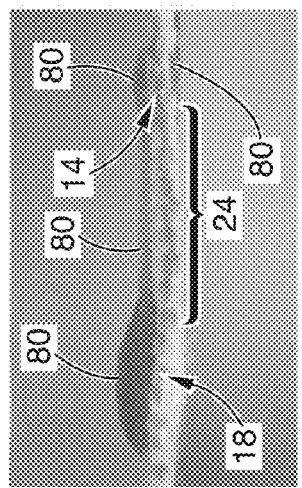
FIG. 8A is an image of the 3D Laplace pressure-driven transport on MST.
Figure 9A:
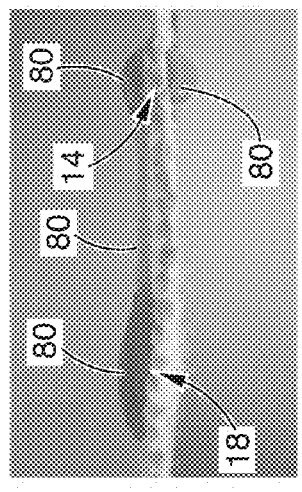
FIG. 9A is an image of the 3D Laplace pressure-driven transport on MST.
Figure 10A:
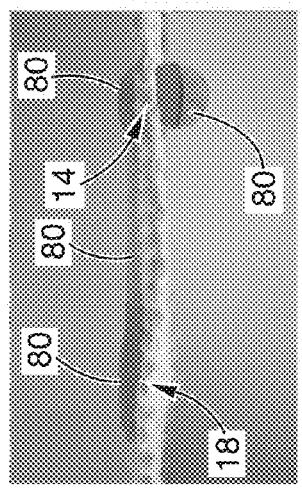
FIG. 10A is an image of the 3D Laplace pressure-driven transport on MST.
Figure 8B:
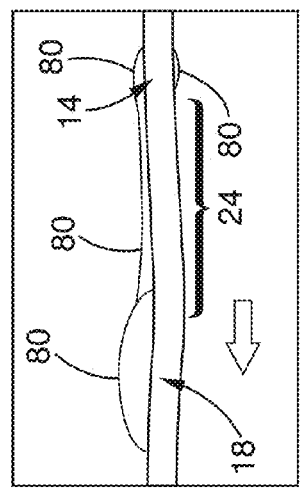
FIG. 8B is a schematic diagram of the 3D Laplace pressure-driven transport on MST.
Figure 9B:
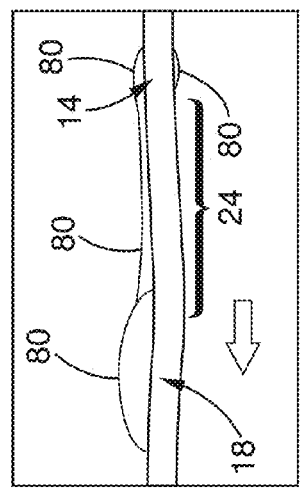
FIG. 9B is a schematic diagram of the 3D Laplace pressure-driven transport on MST.
Figure 10B:
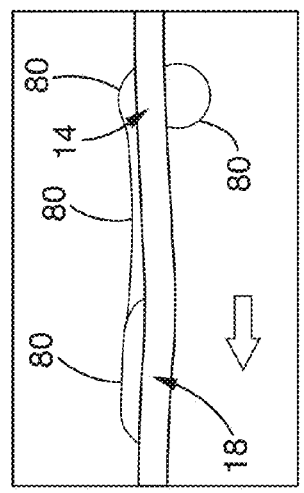
FIG. 10B is a schematic diagram of the 3D Laplace pressure-driven transport on MST.

This Laplace pressure-driven transport can overcome gravitational influence as illustrated in the images 78 of FIG. 8A, 9A and FIG. 10A. Importantly, since the inlet 14 and the outlet 18 reservoirs are fabricated by the unique two-stage stereo-stitching technique as aforementioned, the liquid 80 traverses from one side of the fabric to the other in a well-confined 3D manner, under the superhydrophobic-defined microfluidic geometries. FIG. 8B, FIG. 9B and FIG. 10B are schematic representations of the images 78 in FIG. 8A, 9A and FIG. 10A.

b. Flow Resistance of Hydrophilic Yarns

In addition to the Laplace pressure gradient generated by the surface tension of the curved droplet surfaces, the liquid transport can also be affected by the flow conductance of the connecting hydrophilic yarns. Various structural parameters, including the thread diameter, yarn porosity, and bundled arrangement (single vs. multi-yarn arrangements), could all factor into the flow resistance analysis. In general, a thicker thread with a larger diameter, though possessing a lower flow resistance, is more difficult to form micropatterns with due to the limited resolution. As the primary focus is on building the surface microfluidic networks using all off-the-shelf components, the internal fabric structures (e.g., yarn porosity) were not altered.

Figure 11A:
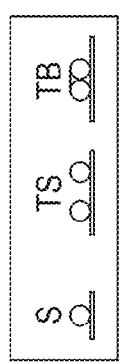
FIG. 11A is a schematic diagram of the cross-sections of yarn structures for single yarn (S), two separated yarns (TS) and a two-yarn bundle (TB) which were analysed for flow resistance.
Figure 11B:
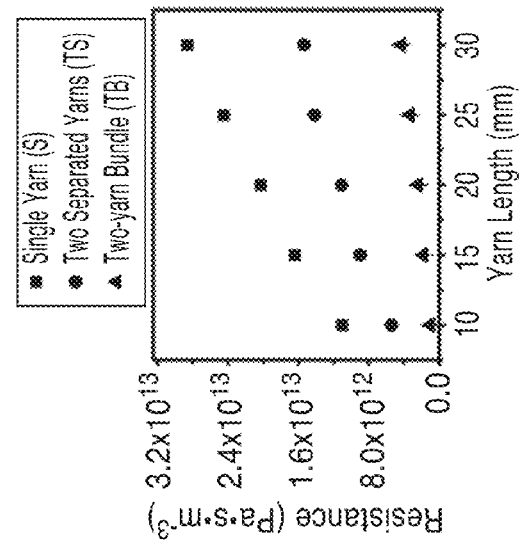
FIG. 11B is a plot of the flow resistance measurement of single yarn (S), two separated yarns (TS) and a two-yarn bundle (TB) at different yarn lengths (from 10 mm to 30 mm).

FIG. 11A through FIG. 13 show the experimental characterizations of the fluid transport on MST. FIG. 11A is a schematic diagram that demonstrates the flow profile on the cross-sections of yarn structures (single yarn (S), two separated yarns (TS) and a two-yarn bundle (TB)). Yarns with an average diameter of 500 μm were utilized for all the measurements. FIG. 11B is a graph which summarizes the experimental investigations on the flow resistance influenced by different fabric configurations and shows the flow resistance measurement of single yarn (S), two separated yarns (TS) and a two-yarn bundle (TB) at different yarn lengths (from 10 mm to 30 mm).

As expected, within the laminar flow region, the flow resistance shows a linear relationship with the length of the fluid flow path. In particular, as the yarn length increases from 10 mm to 30 mm, the flow resistance of a single yarn rises from $1.10 \times 10^{13}$ Pa·s·m$^{-3}$ to $2.86 \times 10^{13}$ Pa·s·m$^{-3}$. However, including additive fluid flow paths in parallel would reduce the flow resistance according to the hydrodynamic theory, which has also been clearly shown in the measurements. If two yarns separated by 5 mm are connected in parallel between droplets, the overall resistance decreases to $5.44 \times 10^{12}$ Pa·s·m$^{-3}$ and $1.56 \times 10^{13}$ Pa·s·m$^{-3}$ for 10 mm and 30 mm long threads, respectively, which are half of the values of resistances for single threads, as predicted.

Notably, a bundled configuration of yarns, i.e., packing two yarns next to each other, would further reduce the flow resistance by a factor of five or more. For instance, at the same yarn length (of 10 mm), the flow resistance of the bundled configuration is measured at $1.04 \times 10^{12}$ Pa·s·m$^{-3}$, which approximates to only one fifth of that of the two separated yarns or 10% of that of the single yarn. This significant improvement on the fluid conductance can be attributed to the different flow profile for the two closely packed yarns.

As can be seen, the flows in the single and separated yarns are all confined by the physical boundaries of the fabrics, similar to the closed-channel microfluidics. Whereas, the bundled arrangement offers a suspended flow region with free-flow boundaries between the two yarns where a minimal liquid-solid contact area is retained under the surface tension, and thus, results in a substantially reduced flow resistance, analogous to the unbounded surface microflow. In brief, the flow resistance is linearly proportional to the length of the hydrophilic yarns and inversely proportional to the number of the separate fluidic pathways in parallel, while a bundled yarn arrangement can lead to an appreciable reduction in the flow resistance under the surface tension-induced suspended flow.

c. Transport Modes: Discrete Versus Continuous Transports

Figure 12A:
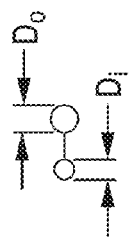
FIG. 12A is a schematic diagram of the diameters of the inlet ($D_i$) and outlet ($D_o$) of the fluid flow path.
Figure 12B:
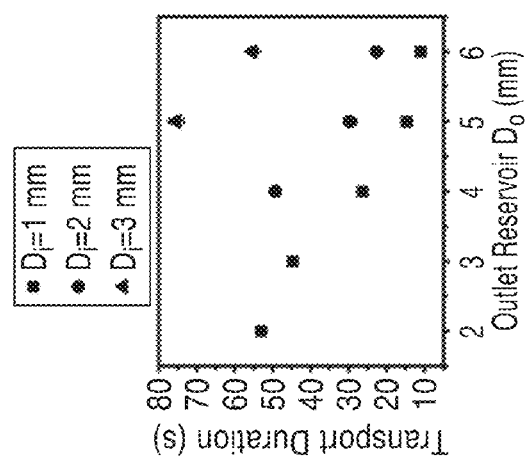
FIG. 12B is a plot of the discrete transport mode—transport duration of a 4 µL droplet on MST with selected single-inlet-single-outlet dimensions ($D_i$ and $D_o$ in diameter, respectively).

In the discrete transport mode, the size difference between the inlet and outlet reservoirs determines the pressure gradient and the pumping rate. In the experimental investigation, the transport durations were measured for various single-inlet-single-outlet configurations, given a fixed droplet volume (of 4 μL). FIG. 12A and FIG. 12B show the selected inlet-outlet dimensions in pairs: 1-2 mm, 1-3 mm, 1-4 mm, 1-5 mm and 1-6 mm; 2-4 mm, 2-5 mm, 2-6 mm; 3-5 mm and 3-6 mm. A two-yarn bundled pattern was utilized as the aqueous-conducting channel with a 10 mm separation between the inlet and outlet.

As expected, the larger outlet leads to an accelerated transport for the same size inlet. For instance, for an inlet of 1 mm in diameter, the transport duration decreases from 53 seconds to 11 seconds as the diameter of outlet extends from 2 mm to 6 mm. This is attributed to the fact that the same liquid droplet possess a lower profile on a larger size reservoir, and thereby, a smaller internal pressure. Conversely, a larger reservoir at the inlet will induce a slower transport given the same outlet dimension. As can be seen, the pump duration increases from 15 seconds to 75 seconds when the inlet reservoir size rises from 1 mm to 3 mm. Moreover, the highest average flow rate of 1.3 mL/h has been achieved at the 1-6 mm configuration. These results have clearly demonstrated the potential of the MST in manipulating flow rates by the micro-stitched geometries.

Figure 13:
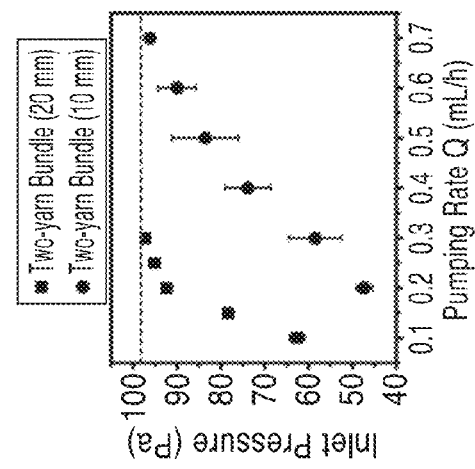
FIG. 13 is a plot of the continuous transport mode—the relationship between the inlet pressure and the constant pumping rate Q with two-yarn bundles (10 mm and 20 mm) as the connection.

In the continuous pumping mode, the Laplace pressure of the droplet at the inlet is directly related to the pumping rate as well as the flow resistance of the channel. FIG. 13 is a graph which demonstrates the measured internal pressure at the inlet as the flow rate varies with different thread/yarn configurations. The diameters of the inlet and outlet are 3 mm and 6 mm, respectively. According to the theoretical analysis, both a higher rate of pumping and a larger channel resistance could result in a larger internal pressure of the droplet. Moreover, the maximal pressure is reached at the inlet when the diameter of the droplet equals the reservoir size (97 Pa for a 3 mm reservoir). These results follow the prediction model well. For example, the average Laplace pressure at the inlet increases from 47 Pa to 96 Pa as the flow rate rises from 0.2 mL/h to 0.6 mL/h, given the fluidic path of 10 mm in length and two-yarn bundled. Furthermore, as the length of the bundle is doubled to 20 mm, the maximum pressure at the inlet of 97 Pa is obtained at 0.3 mL/h, compared with that of 59 Pa for the mm case. Overall, a higher flow rate can be established by yarn structures of a lower flow resistance.

d. Multi-Inlet-Single-Outlet Configuration

The maximal transport rate per unit area can be a critical measure for biofluidic transport applications. As previously discussed, the fluidic characterization of MST is based on a single-inlet-single-outlet (bi-droplet) configuration and a maximal flow rate of 1.3 mL/h was achieved on the MST for a 1-6 mm pattern (given the connecting yarn of 10 mm in length and 500 μm in diameter with bundled structure). The minimal inlet size that can be achieved is limited by the yarn diameter (which is 1 mm in this case), while an outlet of the diameter greater than 6 mm cannot provide noticeable improvement over transport rate according to our measurements, as shown in FIG. 12B.

FIG. 12B is a plot of the discrete transport mode. This plot shows the transport duration of a 4 μL droplet on MST with selected single-inlet-single-outlet dimensions ($D_i$ and $D_o$ in diameter, respectively, see FIG. 12A). FIG. 13 is a plot of the continuous transport mode and shows the relationship between the inlet pressure and the constant pumping rate Q with two-yarn bundles (10 mm and 20 mm) as connection.

Given that the area of the micropattern is approximately 1 cm² (6 mm×17 mm), 1.3 mL/h per cm² was considered the maximal transporting rate achievable by the single-inlet-single-outlet configuration. Further improvement of the unit area transport rate of MST can be achieved by directing several collection spots to a common outlet to form a multi-inlet-single-outlet fluidic transport network (e.g. the fluidic network design in a radial pattern) as shown previously in FIG. 1 and FIG. 3D. Compared with the repeated one-inlet-one-outlet structures, the multi-inlet-single-outlet network design not only reduces the number of the outlets to one, but also improves the utility of the space among adjacent fluidic paths with the radial geometry design, which results in a considerably enhanced unit-area flow rate. For example, 10 individual single-inlet-single-outlet micropatterns (1-6 mm, 10 mm channel length), stitched closely side by side on a textile, would cover an area of about 10 cm² while achieving a maximal flow rate of approximately 1.3 mL·h$^{-1}$·cm$^{-2}$ as measured previously.

Alternatively, by connecting the ten inlets to one common outlet in a radial pattern as shown in FIG. 1, its total footprint is only 6.2 cm² (14 mm in radius). This is 40% more efficient than that of the former design, leading to a higher unit-area transport rate of 2.1 mL·h$^{-1}$·cm$^{-2}$. The multi-inlet-single-outlet design can be significantly more efficient when additional inlets are directed to the shared outlet. However, the maximal number of the inlets to be added would be restrained by the fabrication resolution, i.e. the inlet size and channel width. In summary, a compact multi-inlet-single-outlet network design will further enhance fluid transport rate (per unit area) of the MST, leading to a higher transport capacity in handling a large biofluidic volume in a short period of time.

e. Interfacial Transport Under Gravitational Effects

The above discussions are all based on the simplified situation where the gravitational force is largely ignored, i.e., when the capillary length limits apply. If the gravitational effect is to be considered, two additional phenomena will be included in the analysis: the hydrostatic pressure generated by gravitation and the droplet removal under gravitation.

Figure 14A:
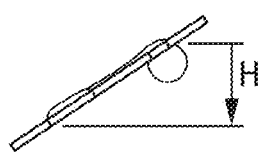
FIG. 14A is a schematic diagram of a height difference between the inlet and outlet when the MST is tilted vertically.
Figure 14B:
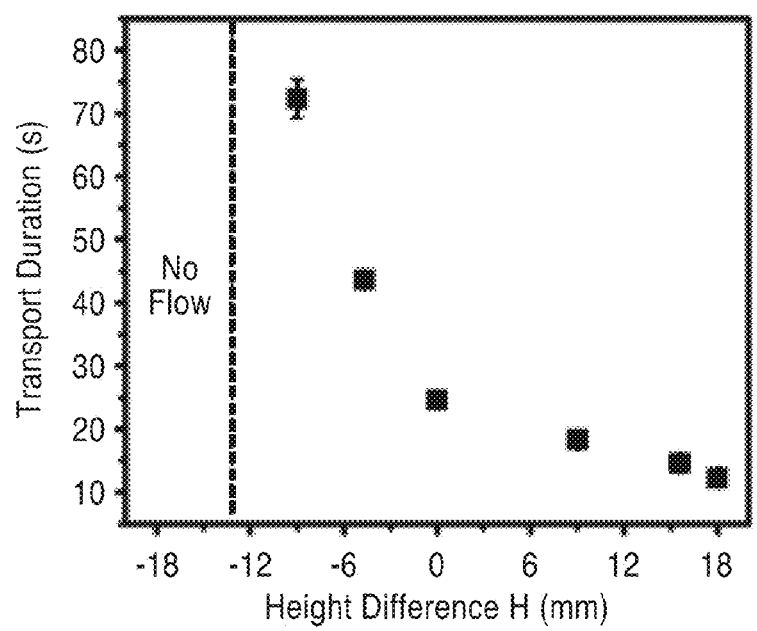
FIG. 14B is a plot of the transport duration of a 4 µL droplet when tilting a 2 mm-6 mm MST to produce a different height difference H between the inlet and outlet.

Whenever the fluidic inlet and outlet are not kept at the same hydrostatic level, the gravitational force will superpose a hydrostatic pressure gradient on the existing Laplace pressure gradient. The combined effects in a single experiment were calibrated by connecting two reservoirs (2 mm-6 mm) through a 10 mm yarn bundle and measuring the transport duration of a 4 μL droplet when tilting the fluidic network to produce various height differences. FIG. 14B shows that at zero height difference (as the chip is positioned horizontally), the transport measurements agree with the previous assessments conducted and shown in FIG. 12B. FIG. 14A shows schematically that the height difference, H, is defined as one end of the inlet to the other end of the outlet in the vertical direction. FIG. 14B shows that as H gradually increases from 0 mm to 18 mm, the transport duration is reduced from 24 seconds to 12 seconds on average, nearly half of the value measured in the horizontal position. However, when the height changes in another direction, for example, under the height difference of 9 mm, the transport time increases to 72 seconds, which is three times slower than that of the horizontal situation.

Continuously increasing the height difference can eventually cease or even reverse the flow. At the height difference of 13 mm, no apparent flow has been observed in either direction, which agrees with the predicted value based on the balance of hydrostatic pressure and Laplace pressure, ΔP in Eq. (1). The gravitation can either promote or reduce the microfluidic transport on the MST by introducing the hydrostatic pressure gradient between the inlet and outlet reservoirs.

Figure 14C:
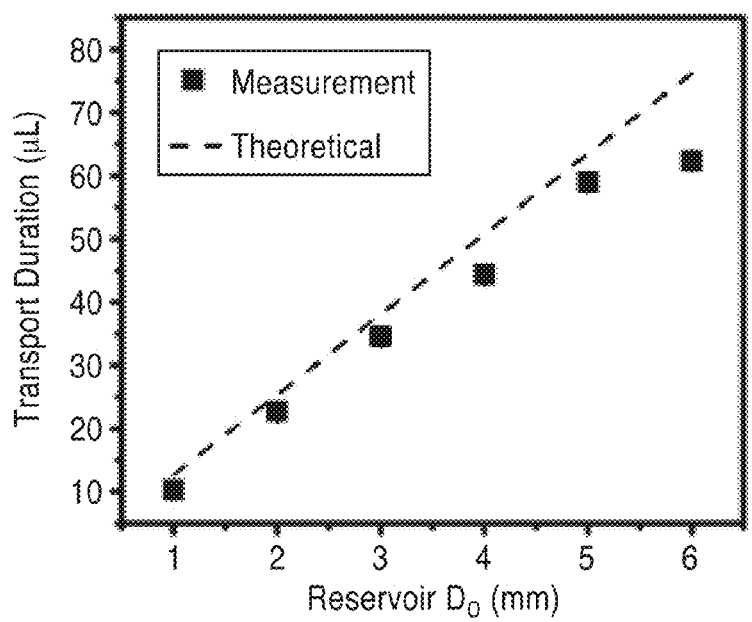
FIG. 14C is a plot of the theoretical prediction and the measurement of the dripping volume on the outlet varying with the diameter $D_o$ of the reservoir.

At the outlet, the droplet can be removed by the gravitational force as its own weight overrides the adhesion to the underside of the hydrophilic fabric. The maximum adhesive force ($F_A$) from a hydrophilic reservoir can be well predicted by the modified Furmidge equation:

$$F_A = D_o \gamma (\cos \theta_R - \cos \theta_A) \quad (3)$$

where γ is the surface tension of the liquid and $\theta_A$ and $\theta_R$ are the advancing and receding angles between the hydrophilic fabric and the underside of the superhydrophobic substrate, respectively. To demonstrate, various sizes of the outlet reservoirs (from 1 mm to 6 mm) were patterned. Subsequently, discrete and continuous flows were both applied to the study. In the discrete flow measurement, the dripping volume of the droplet, which is directly related to the maximum adhesion force $F_A$, follows the diameter of the reservoir in a linear fashion, which has been verified experimentally, and is shown in FIG. 14C. For example, the reservoir of 6 mm in diameter can hold a droplet of up to 62 μL until a droplet is detached and rolls down under the gravitational influence. As the droplets are manually added, disturbance of the droplet pressure can slightly affect the maximal removal rate and lead to deviations between the theoretical predications and experimental measurements. The droplet removal process can reset the pressure inside the outlet reservoir and enable continuous outflow.

V. Demonstration

Sweat Collection and Removal

Sweat is secreted by the sweat glands distributed throughout the human body, which is composed mostly of water with various electrolytes. It serves as a primary means of thermoregulation (i.e., surface cooling), during which evaporation of sweat removes the latent heat from the skin underneath. During intensive physical activities, human sweat loss (or perspiration rate) can be as high as 2-4 liters per hour, equal to an average rate of 0.10 to 0.21 mL·h$^{-1}$·cm$^{-2}$ (provided that the overall skin area of 1.88 m$^2$ for an average male adult). Without efficient sweat removal, accumulative sweat can drastically increase the humidity level surrounding the skin surface, leading to elevated discomfort.

Therefore, fabric designs for sport activities have been focused on rapid removal of sweat and maintaining a low-humidity level on the skin surface. Specifically, natural cotton-based fabric is historically known for its high absorbance of sweat due to its intrinsically hydrophilic nature. However, after cotton-based fabric is fully hydrated, its weight drastically increases while the gas-permittivity sharply decreases creating limited capacity for sweat and humidity removal. The excessive liquid in the cotton makes the fabric wet and creates a heavy, sticky, and cold feeling on the skin. Newer fabric designs, such as Coolmax™ (Invista), utilize specialized polyester fibers with irregular woven cross-sections (known as tetra- or hexa-channels) to achieve efficient body moisture control. In principle, the smaller microchannels inside generate capillary force (in the order of 1 kPa) to extract the sweat and spread the fluid over a large area of the exterior fabric for facilitated evaporation. Meanwhile, the inter-fiber gap allows more air circulation and less moisture level on the skin surface for a comfortable and breathable sensation. However, the capillary-based absorption and evaporation are still subject to environmental temperature and humidity, and moreover, the fabric becomes heavier and less efficient under extensive perspiration conditions.

Figure 15A:
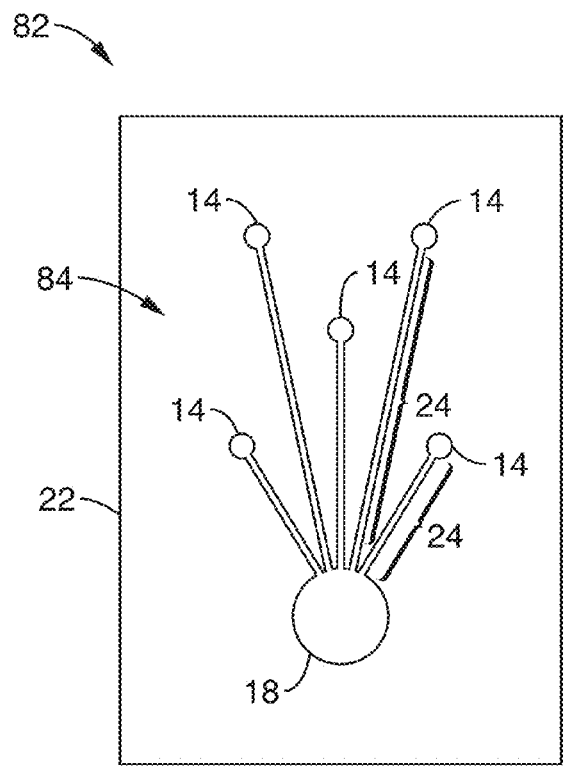
FIG. 15A is a schematic diagram of the front side of the MST for sweat collection and removal.
Figure 15B:
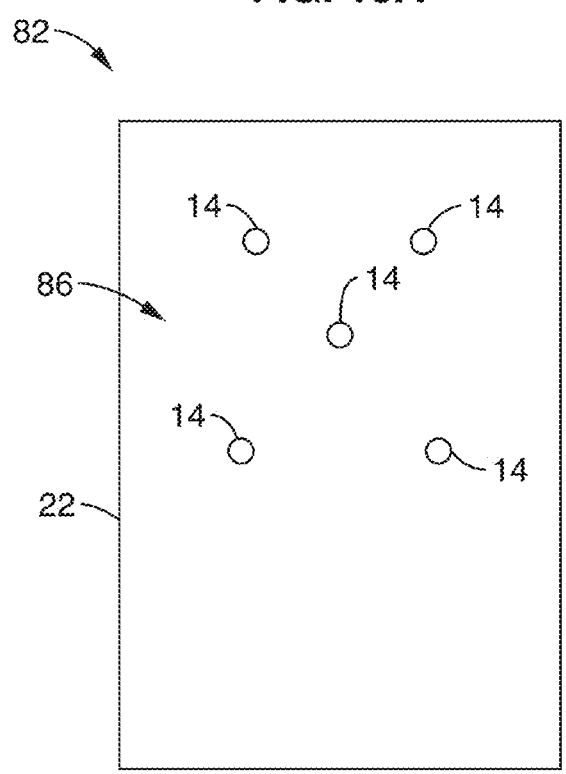
FIG. 15B is a schematic diagram of the back side of the MST for sweat collection and removal.

Accordingly, an artificial skin model was fabricated for demonstration of the MST using the method aforementioned for high-efficiency sweat management (see FIG. 4A and FIG. 4B). Referring now to FIG. 15A and FIG. 15B, a micro-stitched pattern with a 1 mm inlet 14 and a 6 mm outlet 18 in a compact 5-inlet-1-outlet MST design 82 was utilized for efficient sweat removal. Both of the transport modes were applied to the MST design 82, in addition to the gravitational effect, during the test. FIG. 15A shows the outer surface of the MST in contact with the outside 84 and FIG. 15B shows the inner surface of the MST in contact with the artificial skin model 86.

Now referring to FIG. 16A through FIG. 16D and FIG. 17A through FIG. 17D, as the human body keeps an up-right position throughout most of the day, it was reasonable to conduct our sweating collection from the outer MST surface 84 by placing the artificial skin model 48 vertically (75°). In the discrete mode, the substrate of the inner MST 86 is periodically put in contact with the artificial sweating surface of the artificial skin model 48 as shown in FIG. 16B and FIG. 16D. As can be seen in FIG. 15A and FIG. 15B, only the 5 inlet 14 collection sites are shown on both the front (outer surface 84) and backside (inner surface 86), which are in contact with the skin, while the conducting hydrophilic yarns 20 and outlet 18 reservoir are on the other side for liquid transport and removal. It has been observed that in each attaching and detaching cycle to the artificial skin model 48, additional volumes are added and absorbed onto the hydrophilic inlets 14, gradually transported to the outer surface 84 of the fabric, and eventually, collected at the outlet 18 opening under the Laplace pressure gradient imposed by the curved droplet surface. This 3D transport, enabled by the wetting contrast, ensures the unidirectional transport and the dryness on the MST surface that is in contact with the skin 86.

After repetitive cycles of droplet collection and removal at the inlets 14, collections from the multiple inlets 14 merge into a big droplet 16 at the outlet 18, which detaches from the fabric as it overweighs the adhesion to the surface as shown in FIG. 16D.

In the continuous transport mode, illustrated by FIG. 17A through FIG. 17D, the MST 82 was placed in close contact with the artificial skin model 48 and fixed by an adhesive tape (Scotch®, 3M). As shown in FIG. 17B, water adsorbed onto the hydrophilic inlets 14 is gradually transported to the outer surface 84 of the fabric 82 from the inner surface. Eventually, the water collects at the outlet 18 opening under the Laplace pressure gradient imposed by the curved droplet surface as seen in FIG. 17C.

As can be seen in FIG. 17D, similar to the phenomenon illustrated in the discrete mode, large droplets 16 consecutively form at the outlet 18 and drip off during the continuous pumping, while the superhydrophobic MST 82 remains dry and gas-permeable.

In order to quantitatively characterize the unique liquid transport performance of MST in the demonstration, several important parameters of a fabric were experimentally investigated, including the thickness, weight, electrical resistance, and gas permeability before and after the textile was completely wetted. Commercial cotton and CoolMax™ fabrics with the same surface area were prepared and tested as a comparison. The results are summarized in Table 1. As can be seen, the original thickness of the MST is comparable to that of the CoolMax™, but greater than the conventional cotton fabrics. Under completely wet conditions, the average weight per unit area of CoolMax™ varies from 0.0282 g·cm$^{-2}$ to 0.1156 g·cm$^{-2}$ (about 310% weight change) due to the high aqueous absorbance of the hydrophilic textile structures, which was similarly found in conventional cotton fabrics. Meanwhile, MST only shows a marginal increment of its unit area weight, from 0.0393 g·cm$^{-2}$ to 0.0544 g·cm$^{-2}$, representing a 43% increase from its initial weight. The significant difference in weight change is contributed to the unique pattern-defined wettability of the MST, which was verified by the electrical resistance measurement in both wettable and non-wettable regions.

Under dry conditions, all three fabrics present open-circuit impedance. After full wetting, both the resistances of the cotton and CoolMax™ fabrics decreased to 0.21 MΩ throughout the entire fabric, which indicates a uniform distribution of a high water content present inside these fabrics. In contrast, the resistance of MST varies over the wettable and non-wettable regions. In particular, the resistance of the micropatterned hydrophilic region, covering only 4% of the entire inner surface, changed from an open circuit impedance to 0.86 MΩ, while the rest of the superhydrophobic MST fabric substrate maintained a high electrical resistance of 116 MΩ (which is believed to be caused by water moisture condensed inside the superhydrophobic fabric). In another measurement, it was found that the gas permittivity of MST (574.5 kPa·s·m$^{-3}$) under a completely wetting condition was substantially lower than that of the cotton and CoolMax™, which was 3186.5 kPa·s·m$^{-3}$ and 4336.5 kPa·s·m$^{-3}$, respectively (given that a forced air flow of 60 ft/m was constantly applied to the fabric surfaces).

The experimental measurements confirmed that the MST remains dry over the majority of the surface area and sustains high gas permittivity within a highly humid environment. Noticeably, this fluidic transport mechanism on MST is completely spontaneous and can be sustainable even under the wettest conditions, and more importantly, it is independent of the ambient temperature and humidity, unlike the conventional fabrics. This feature can be highly advantageous in conditions of heavy perspiration in humid weather, which is essential for the comfort of the human body during intensive exercise. In addition, the utility of the interfacial microfluidic transport on the MST can be extended to similar biofluidic transport applications, e.g., urine removal or collection, and drainage of wound exudates. Overall, the MST enables a surface tension-driven flow for controlled and facilitated transport of fluids on wettability-patterned textile surfaces.

VI. Conclusions

An interfacial microfluidic transport model has been presented and implemented on micropatterned superhydrophobic textiles (MST). The MST platform, utilizing the extreme wetting contrast between very hydrophilic yarns and a superhydrophobic textile substrate, confines the aqueous flow pathway and enables autonomous surface tension-driven microflow on the textile surface. As compared to the previously reported textile-based microfluidic systems, it is capable of achieving a continuous flow in a highly controllable manner without an external pumping system (e.g., capillary or syringe pumps). The maximal flow rate achieved by the MST after becoming completely wet was 1.3 mL/h (21 μL/min) in a discrete mode which is higher than reported capillary pumps and it can be continuously achieved even after the yarn is completely wet, under which the capillary/wicking force would eventually cease working.

Two 3D operation modes, discrete and continuous transports, have been introduced. By a unique two-stage stereostitching approach on the spray-coated superhydrophobic cotton fabric (CA=140±3), various micropattern designs (from diameters of 1 mm to 6 mm) have been fabricated and tested. In addition, the flow resistance on the hydrophilic pathway has also been modeled and evaluated. Measurements of flow resistance on single or multiple yarn configurations have been compared and analyzed, from which a closely packed bundle arrangement leads to the highest flow conductance due to formation of the surface tension-induced free flow region. Together, the MST system can provide a repeatable flow rate up to 1.3 mL/h.

Finally, its applicability toward facilitated and controlled biofluid removal, such as skin surfaces experiencing heavy perspiration, was demonstrated. As one of the main innovations, the MST continuously removes the sweat by collecting the moistures from the skin surface, transports the fluidic contents to the exterior surface, and collects them into miniature droplets, which can eventually, without friction roll over on the superhydrophobic surface once their weights exceed the adhesion to the substrate. In fact, during this process, the MST maintains extremely low humidity and ultrahigh air permittivity, unlike the conventional fabrics, and therefore, it allows significantly improved evaporation process on human skin. In summary, the intriguing interfacial microfluidics, established on MST, offers a novel autonomous means to manipulate aqueous flow on a textile platform, which can be readily utilized for industrial manufacturing, and can be further extended to biofluid transport applications, which require high-efficiency and controlled fluidic flow.

The present invention is a new type of textile construction that is able to transport liquid on the skin's surface to the outer side of a fabric, where the liquid collects and drips off. The textile utilizes interfacial microfluidic principles and implements liquid transport spontaneously using hydrophilic micropatterns on a superhydrophobic/hydrophobic fabric surface. The invention provides a new dimension of transport to the textile: surface tension force, in addition to intrinsic capillary force in hydrophilic fibers. The invention exhibits several novel features which include, but are not limited to, the following: (1) Applies interfacial/surface microfluidics principle to body fluidic transport; (2) Facilitates body fluid removal; (3) Models microfluidic transport on patterned hydrophobic and superhydrophobic fabrics; (4) Provides well controlled flow rate and removal rate of the fluid; (5) Is capable of both moisture and liquid removal due to patterned wettability; (6) Uses a fabrication process that is simple and compatible with the large-scale cloth manufacturing; and (7) Is self-cleaning and waterproof.

VII. Alternative Embodiments

The subject invention material comprises hydrophilic yarn and hydrophobic fabrics, which is distinguished by the contact angle (CA). A material's CA smaller than 90 degrees is hydrophilic while a CA larger than 90 degrees is hydrophobic. Several common materials are listed in both categories and any combination from these two categories can form the MST structure in the application.

The hydrophilic yarn can comprise, for example, cotton, nylon, hemp, polyester, etc. The hydrophobic fabrics can comprise, for example, grafted nylon fabric, hydrophobic material coated cotton and wool, non-wetting silk, etc.

Figure 18A:
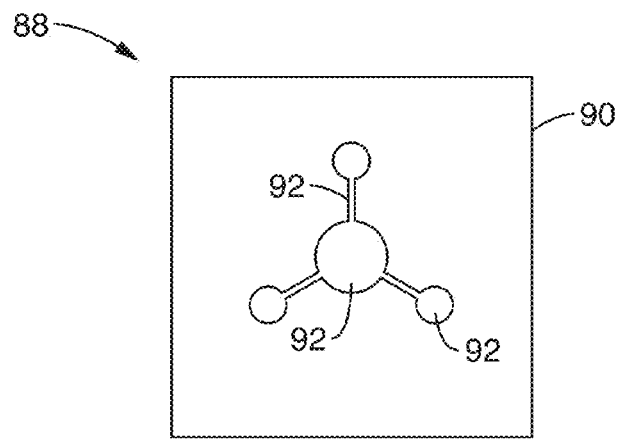
FIG. 18A and FIG. 18B are schematic diagrams of an alternative design of MST.
Figure 18B:
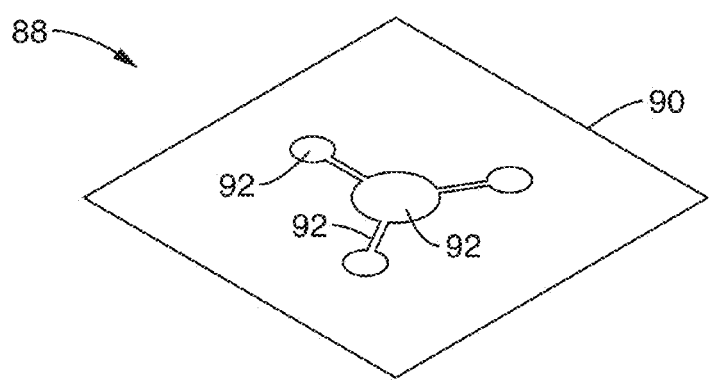
Figure 18C:
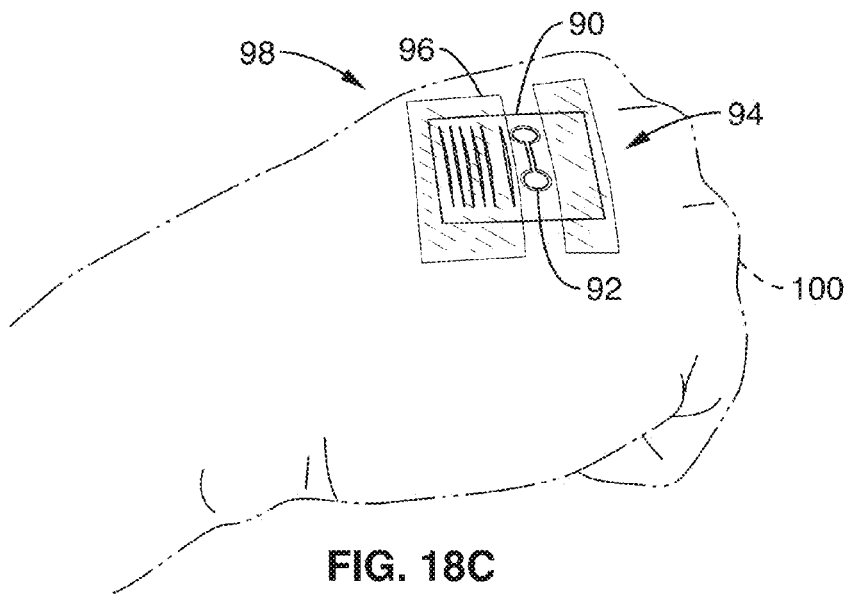
FIG. 18C is schematic diagram of a preliminary test of an alternative design of MST on skin.

An alternative design of MST 88 is illustrated in FIG. 18A, FIG. 18B and FIG. 18C. It comprises a thin layer of hydrophobic material 90, on which channel-like patterns 92 are cut and formed. This material can be fixed on the skin 94 under compression with adhesive tape 96 or any equivalent thereof. FIG. 18C shows a schematic diagram 98 of a human hand 100 with the alternative design of MST 88 fixed on the skin 94. Since the human skin 94 is hydrophilic by nature, the bottom skin surface serves as the hydrophilic substrate for the alternative design MST 88 and the boundary of the channel is defined by the patterned hydrophobic material 90. According to preliminary tests, microflow similar to the process previously described can be established with this new alternative design of MST 88.

In summary, the start shape of the MST has a minimum of only one fluid flow path, with one inlet and one outlet. The more fluid flow paths in one design, the more efficient the unit area transport rate. The maximum number of fluid flow paths in one design depends on the resolution of the stitching technique.

From the discussion above it will be appreciated that the invention can be embodied in various ways, including the following:

1. A method of transporting fluid on a fabric, the method comprising: (a) creating a fluid flow path on a hydrophobic fabric; (b) wherein said fluid flow path comprises a hydrophilic material; (c) wherein said fluid flow path comprises an inlet and an outlet connected by a channel; (d) wherein said fluid flows continuously and autonomously along said fluid flow path; and (e) wherein said fluid flow is not affected by the absorption ability of the fabric and environmental humidity.

2. The method of any preceding embodiment, wherein the hydrophobic fabric has a fluid contact angle of at least 90°.

3. The method of any preceding embodiment, wherein the hydrophobic fabric has a fluid contact angle of between 90° and 140°.

4. The method of any preceding embodiment, wherein said hydrophilic material has a fluidic contact angle smaller than 90°.

5. The method of any preceding embodiment, wherein said inlet and said outlet can accumulate fluid to form a curved fluid surface.

6. The method of any preceding embodiment, wherein said channel comprises single threads or thread bundles.

7. The method of any preceding embodiment, wherein said outlet is larger than said channel.

8. The method of any preceding embodiment: (a) wherein the hydrophobic fabric comprises a first surface and a second surface; (b) wherein the inlet is formed throughout the hydrophobic fabric such that the inlet is present on the first surface and the second surface; (c) wherein the channel and the outlet are formed on the hydrophobic fabric such that the channel and the outlet are only present on the second surface of the hydrophobic fabric; and (d) wherein when a fluid contacts the inlet, the fluid is transported from the first surface to the second surface, along the channel and to the outlet.

9. The method of any preceding embodiment, wherein the continuous and autonomous fluid flow is maintained by the Laplace Pressure of liquid.

10. The method of any preceding embodiment, wherein the fluid can be removed from said outlet by droplet formation and dripping.

11. The method of any preceding embodiment, wherein a plurality of said hydrophilic fluid flow paths are configured to flow and terminate at one or more said outlets, creating a fluidic network design.

12. The method of any preceding embodiment, wherein a plurality of said fluidic network designs are configured on a piece of wearable hydrophobic fabric.

13. A method of transporting fluid across skin, the method comprising: (a) cutting a hollow pattern in a hydrophobic fabric; and (b) fixing said patterned hydrophobic fabric to skin; (c) wherein said skin forms a hydrophilic fluid flow path; (d) wherein said fluid flow path comprises an inlet and an outlet connected by a channel for said fluid; (e) wherein said fluid flows continuously and autonomously along said fluid flow path; and (f) wherein said fluid flow is not affected by environmental humidity.

14. The method of any preceding embodiment, wherein the hydrophobic fabric has a fluid contact angle of at least 90°.

15. The method of any preceding embodiment, wherein the hydrophobic fabric has a fluid contact angle of between 90° and 140°.

16. The method of any preceding embodiment, wherein said inlet and outlet can accumulate fluid to form a curved fluid surface.

17. The method of any preceding embodiment, wherein said outlet is larger than said channel.

18. The method of any preceding embodiment, wherein the continuous and autonomous fluid flow is maintained by the Laplace Pressure of liquid.

19. The method of any preceding embodiment, wherein the fluid can be removed from said outlet by droplet formation and dripping.

20. The method of any preceding embodiment, wherein a plurality of said hydrophilic fluid flow paths are configured to flow and terminate at one or more said outlets, creating a fluidic network design.

21. The method of any preceding embodiment, wherein a plurality of said fluidic network designs are configured on a piece of wearable hydrophobic fabric.

22. A fabric capable of transporting fluids, the fabric comprising: (a) a hydrophobic fabric material; and (b) a fluid flow path formed on said hydrophobic fabric material; (c) wherein said fluid flow path comprises a hydrophilic material; (d) wherein said fluid flow path comprises an inlet and an outlet connected by a channel; (e) wherein said fluid flows continuously and autonomously along said fluid flow path; and (f) wherein said fluid flow is not affected by the absorption ability of the fabric environmental humidity.

23. The fabric of any preceding embodiment, wherein the hydrophobic fabric has a fluid contact angle of at least 90°.

24. The fabric of any preceding embodiment, wherein the hydrophobic fabric has a fluid contact angle of between 90° and 140°.

25. The fabric of any preceding embodiment, wherein said hydrophilic material has a fluidic contact angle smaller than 90°.

26. The fabric of any preceding embodiment, wherein said inlet and outlet can accumulate fluid to form a curved fluid surface.

27. The fabric of any preceding embodiment, wherein said channel comprises single threads or thread bundles.

28. The fabric of any preceding embodiment, wherein said outlet is larger than said channel.

29. The fabric of any preceding embodiment: (a) wherein the hydrophobic fabric comprises a first surface and a second surface; (b) wherein the inlet is formed throughout the hydrophobic fabric such that the inlet is present on the first surface and the second surface; (c) wherein the channel and the outlet are formed on the hydrophobic fabric such that the channel and the outlet are only present on the second surface of the hydrophobic fabric; and (d) wherein when a fluid contacts the inlet, the fluid is transported from the first surface to the second surface, along the channel and to the outlet.

30. The fabric of any preceding embodiment, wherein the continuous and autonomous fluid flow is maintained by the Laplace Pressure of liquid.

31. The fabric of any preceding embodiment, wherein the fluid can be removed from said outlet by droplet formation and dripping.

32. The fabric of any preceding embodiment, wherein a plurality of said hydrophilic fluid flow paths are configured to flow and terminate at one or more said outlets, creating a fluidic network design.

33. The fabric if any preceding embodiment, wherein a plurality of said fluidic network designs are configured on a piece of wearable hydrophobic fabric.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

In addition to any other claims, the applicant(s)/inventor(s) claim each and every embodiment of the invention described herein, as well as any aspect, component, or element of any embodiment described herein, and any combination of aspects, components or elements of any embodiment described herein.

(e) wherein said fluid flow is not affected by the absorption ability of the fabric and environmental humidity;
(f) wherein the hydrophobic fabric comprises a first surface and a second surface;
(g) wherein the inlet is formed throughout the hydrophobic fabric such that the inlet is present on the first surface and the second surface;
(h) wherein the channel and the outlet are formed on the hydrophobic fabric such that the channel and the outlet are only present on the second surface of the hydrophobic fabric; and
(i) wherein when a fluid contacts the inlet, the fluid is transported from the first surface to the second surface, along the channel to the outlet.

2. The method of claim 1, wherein the hydrophobic fabric has a fluid contact angle of at least 90°.

3. The method of claim 1, wherein the hydrophobic fabric has a fluid contact angle of between 90° and 140°.

4. The method of claim 1, wherein said hydrophilic material has a fluidic contact angle smaller than 90°.

5. The method of claim 1, wherein said inlet and said outlet can accumulate fluid to form a curved fluid surface.

6. The method of claim 1, wherein said channel comprises single threads or thread bundles.

7. The method of claim 1, wherein said outlet is larger than said channel.

8. The method of claim 1, wherein the continuous and autonomous fluid flow is maintained by the Laplace Pressure of liquid.

9. The method of claim 1, wherein the fluid can be removed from said outlet by droplet formation and dripping.

10. The method of claim 1, wherein a plurality of said hydrophilic fluid flow paths are configured to flow and terminate at one or more said outlets, creating a fluidic network design.

11. The method of claim 10, wherein a plurality of said fluidic network designs are configured on a piece of wearable hydrophobic fabric.

12. A method of transporting fluid across skin, the method comprising:
(a) forming a pattern of open channels in a hydrophobic material, the channels having hydrophobic side surfaces;

TABLE 1

Comparison of wetting characteristics among cotton, CoolMax ™ and MST.

| Textile Type | Thickness (mm) | Original Weight (g/cm$^2$) | Wetted Weight (g/cm$^2$) | Original Electrical Resistance ($\Omega$)† | Wetted Electrical Resistance (M$\Omega$)† | Original Gas Permeability (kPa · s · m$^{-3}$)‡ | Wetted Gas Permeability (kPa · s · m$^{-3}$)‡ |
|---|---|---|---|---|---|---|---|
| Cotton | 0.260 | 0.0181 ± 0.0040 | 0.0843 ± 0.0100 | Open Circuit | 0.21 ± 0.02 | N/A | 3186.5 ± 52.5 |
| CoolMax ™ | 0.470 | 0.0282 ± 0.0020 | 0.1156 ± 0.0100 | Open Circuit | 0.21 ± 0.01 | N/A | 4336.5 ± 157.0 |
| MST | 0.550 | 0.0393 ± 0.0020 | 0.0544 ± 0.0100 | Open Circuit | Micropatterns (4%): 0.86 ± 0.65 SH substrate (96%): 116 ± 22 | N/A | 574.5 ± 52.0 |

†The resistance data were measured between 2 points 3 mm apart from each other on the side in contact with the artificial skin.
‡The gas resistance was measured by passing gas flow at 60 ft/min through a circular piece of textile with diameter of 2 cm; the gas permeability of dry textile is too small to be accurately measured by the setup.

What is claimed is:

1. A method of transporting fluid on a fabric, the method comprising:
(a) creating a fluid flow path on a hydrophobic fabric;
(b) wherein said fluid flow path comprises a hydrophilic material;
(c) wherein said fluid flow path comprises an inlet and an outlet connected by a channel;
(d) wherein said fluid flows continuously and autonomously along said fluid flow path;

(b) fixing the channels of the patterned hydrophobic material to skin closing one side the channels forming a channel bottom; and (c) coupling an inlet and an outlet to each of the channels;

(d) wherein said skin forms a hydrophilic fluid flow path within the channels from the inlet to the outlet;

(e) wherein fluid flows continuously and autonomously along said fluid flow path; and (f) wherein fluid flow is not affected by environmental humidity.

13. The method of claim 12, wherein the hydrophobic material has a fluid contact angle of at least 90°.

14. The method of claim 12, wherein the hydrophobic material has a fluid contact angle of between 90° and 140°.

15. The method of claim 12, wherein said inlet and outlet can accumulate fluid to form a curved fluid surface.

16. The method of claim 12, wherein said outlet is larger than said channel.

17. The method of claim 12, wherein the continuous and autonomous fluid flow is maintained by the Laplace Pressure of liquid.

18. The method of claim 12, further comprising:
forming droplets on an outlet surface;
wherein fluid can be removed from the outlet by droplet formation and dripping.

19. The method of claim 12, wherein a plurality of said hydrophilic fluid flow paths are configured to flow and terminate at one or more said outlets, creating a fluidic network design.

20. The method of claim 19, wherein a plurality of said fluidic network designs are configured on a piece of wearable hydrophobic fabric.

21. A fabric capable of transporting fluids, the fabric comprising:

(a) a hydrophobic fabric material with a first surface and a second surface; and (b) a fluid flow path formed on the hydrophobic fabric material;

(c) wherein the fluid flow path comprises a hydrophilic material;

(d) wherein the fluid flow path comprises an inlet and an outlet connected by a channel;

(e) wherein the inlet is formed throughout the hydrophobic fabric such that the inlet is present on the first surface and the second surface;

(f) wherein the channel and the outlet are formed on the hydrophobic fabric such that the channel and the outlet are only present on the second surface of the hydrophobic fabric;

(g) wherein when a fluid contacts the inlet, the fluid is transported from the first surface to the second surface, along the channel and to the outlet;

(h) wherein fluid flows continuously and autonomously along the fluid flow path; and (i) wherein fluid flow is not affected by the absorption ability of the fabric environmental humidity.

22. The fabric of claim 21, wherein the hydrophobic fabric has a fluid contact angle of at least 90°.

23. The fabric of claim 21, wherein the hydrophobic fabric has a fluid contact angle of between 90° and 140°.

24. The fabric of claim 21, wherein said hydrophilic material has a fluidic contact angle smaller than 90°.

25. The fabric of claim 21, wherein said inlet and outlet can accumulate fluid to form a curved fluid surface.

26. The fabric of claim 21, wherein said channel comprises single threads or thread bundles.

27. The fabric of claim 21, wherein said outlet is larger than said channel.

28. The fabric of claim 21, wherein a plurality of said hydrophilic fluid flow paths are configured to flow and terminate at one or more said outlets, creating a fluidic network design.

29. The fabric of claim 28, wherein a plurality of said fluidic network designs are configured on a piece of wearable hydrophobic fabric.

* * * * *